US012083215B2

(12) United States Patent
Ostrovski et al.

(10) Patent No.: US 12,083,215 B2
(45) Date of Patent: Sep. 10, 2024

(54) TARGETED DELIVERY OF AEROSOLS OF MAGNETIZED ACTIVE AGENTS

(71) Applicant: TECHNION RESEARCH & DEVELOPMENT FOUNDATION LIMITED, Haifa (IL)

(72) Inventors: Yan Ostrovski, Beer-Sheva (IL); Josue Sznitman, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 112 days.

(21) Appl. No.: 17/329,254

(22) Filed: May 25, 2021

(65) Prior Publication Data

US 2021/0283048 A1    Sep. 16, 2021

Related U.S. Application Data

(62) Division of application No. 16/096,374, filed as application No. PCT/IL2017/050472 on Apr. 25, 2017, now Pat. No. 11,013,682.

(60) Provisional application No. 62/327,324, filed on Apr. 25, 2016.

(51) Int. Cl.
| | |
|---|---|
| *A61K 9/00* | (2006.01) |
| *A61M 15/00* | (2006.01) |
| *A61M 16/10* | (2006.01) |
| *A61N 2/00* | (2006.01) |

(52) U.S. Cl.
CPC .......... *A61K 9/0009* (2013.01); *A61K 9/0073* (2013.01); *A61M 15/009* (2013.01); *A61M 16/10* (2013.01); *A61N 2/002* (2013.01)

(58) Field of Classification Search
CPC . A61K 9/0009; A61K 9/0073; A61M 15/009; A61M 16/10; A61N 2/002
See application file for complete search history.

(56) References Cited

U.S. PATENT DOCUMENTS

| | | | |
|---|---|---|---|
| 4,101,435 | A | 7/1978 | Hasegawa et al. |
| 4,208,294 | A | 6/1980 | Khalafalla et al. |
| 4,554,088 | A | 11/1985 | Whitehead et al. |
| 4,554,089 | A | 11/1985 | Umemura et al. |
| 8,534,277 | B2 | 9/2013 | Stenzler et al. |
| 2009/0299127 | A1 | 12/2009 | Rudolph et al. |
| 2012/0108676 | A1* | 5/2012 | Smyth ................ C08B 37/0084 977/773 |

FOREIGN PATENT DOCUMENTS

| | | |
|---|---|---|
| DE | 19624426 A1 | 1/1998 |
| EP | 2022525 A1 | 2/2009 |
| WO | 2002000870 A2 | 1/2002 |

OTHER PUBLICATIONS

Frederic Tewes et al: "Superparamagnetic iron oxide nanoparticles (SPIONs)-loaded Trojan 5 microparticles for targeted aerosol delivery to the lung", European Journal of Pharmaceutics and Biopharmaceutics, vol. 86, Issue 1, Jan. 2014, pp. 98-104.

Andrew R. Martin et al: "Enhanced deposition of high aspect ratio aerosols in small airway bifurcations using magnetic field alignment", Journal of Aerosol Science, vol. 39, Issue 8, Aug. 2008, pp. 679-690.

Petra Dames et al: "Targeted delivery of magnetic aerosol droplets to the lung". Nature Nanotechnology, vol. 2, No. 8, pp. 495-499, Aug. 2007.

Joseph D. Brain et al: "Correlation between the behavior of magnetic iron oxide particles in the lungs of rabbits and phagocytosis", Experimental Lung Research, vol. 6, issue 2, pp. 115-131, 1984.

Marie-France Bellin: "MR contrast agents, the old and the new", European Journal of Radiology, vol. 60, issue 3, Dec. 2006, pp. 314-323.

Saito Kazuhiro et al: "Perfusion study of hypervascular hepatocellular carcinoma with SPIO", Magnetic Resonance in Medical Sciences, vol. 4, No. 4, pp. 151-158, 2005.

Yuanyuan Xie et al: "In vitro and in vivo lung deposition of coated magnetic aerosol particles", Journal of Pharmaceutical Sciences, vol. 99, No. 11, pp. 4658-4668, 2010.

Gillian E. S. Redman et al: "Pilot Study of Inhaled Aerosols Targeted via Magnetic Alignment of High Aspect Ratio Particles in Rabbits", Journal of Nanomaterials, vol. 2011, pp. 1-7, 2011.

Jinxiang Xi et al: "Improving intranasal delivery of neurological nanomedicine to the olfactory region using magnetophoretic guidance of microsphere carriers", International Journal of Nanomedicine, vol. 10, No. 10, pp. 1211-1222, Feb. 2015.

Oveis Pourmehran et al: "Simulation of magnetic drug targeting through tracheobronchial airways in the presence of an external non-uniform magnetic field using Lagrangian magnetic particle tracking", Journal of Magnetism and Magnetic Materials, vol. 393, Nov. 1, 2015, pp. 380-393.

(Continued)

*Primary Examiner* — Robert S Cabral
(74) *Attorney, Agent, or Firm* — The Roy Gross Law Firm, LLC; Roy Gross

(57) ABSTRACT

The invention provides compositions, kits and methods for depositing a composition comprising a plurality of magnetic particles, to a target site of a subject by delivering the composition via controlled inhalation to a region of the subject's respiratory tract and applying a magnetic field to a target site within the region of the subject's respiratory tract to capture the particles in said target site.

19 Claims, 8 Drawing Sheets

(56) References Cited

OTHER PUBLICATIONS

R.C. Martinez et al: "Simulation of enhanced deposition due to magnetic field alignment of ellipsoidal particles in a lung bifurcation", Journal of Aerosol Medicine and Pulmonary Drug Delivery, vol. 26, No. 1, pp. 31-40, May 2012.
Andrej Krafcik et al: "Computational analysis of magnetic field induced deposition of magnetic particles in lung alveolus in comparison to deposition produced with viscous drag and gravitational force", Journal of Magnetism and Magnetic Materials, vol. 380, 2015, pp. 46-53.
J. W. Haverkort et al: "Computational simulations of magnetic particle capture in arterial flows", Annals of Biomedical Engineering, vol. 37, No. 12, Dec. 2009, pp. 2436-2448.
J. L. Zhang et al: "Core-shell magnetite nanoparticles surface encapsulated with smart stimuli-responsive polymer: Synthesis, characterization, and LCST of viable drug-targeting delivery system", Langmuir, vol. 23, pp. 6342-6351, Apr. 27, 2007.
Pubudu M. Peiris et al: "Enhanced delivery of chemotherapy to tumors using a multicomponent nanochain with radio-frequency-tunable drug release", ACS Nano vol. 6, No. 5, pp. 4157-4168, Apr. 9, 2012.
Quanliang Cao et al: "Enhancement of the efficiency of magnetic targeting for drug delivery: Development and evaluation of magnet system", Journal of Magnetism and Magnetic Materials, vol. 323, No. 15, 2011, pp. 1919-1924.
International Search Report PCT/IL2017/050472 Completed Jul. 30, 2017; Mailed Aug. 1, 2017 3 pages.
Written Opinion of the International Searching Authority PCT/IL2017/050472 Mailed Aug. 1, 2017 7 pages.

* cited by examiner

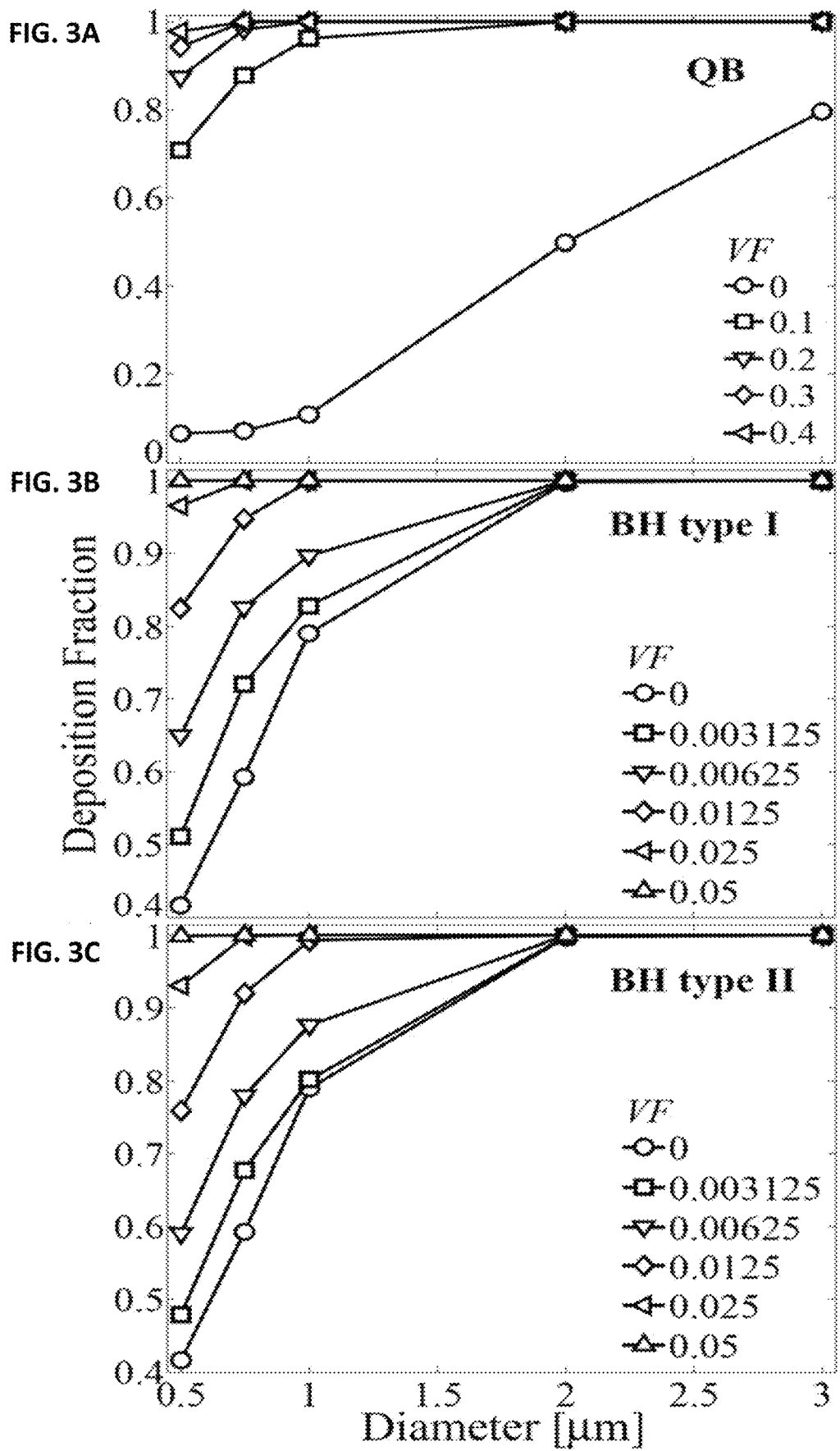

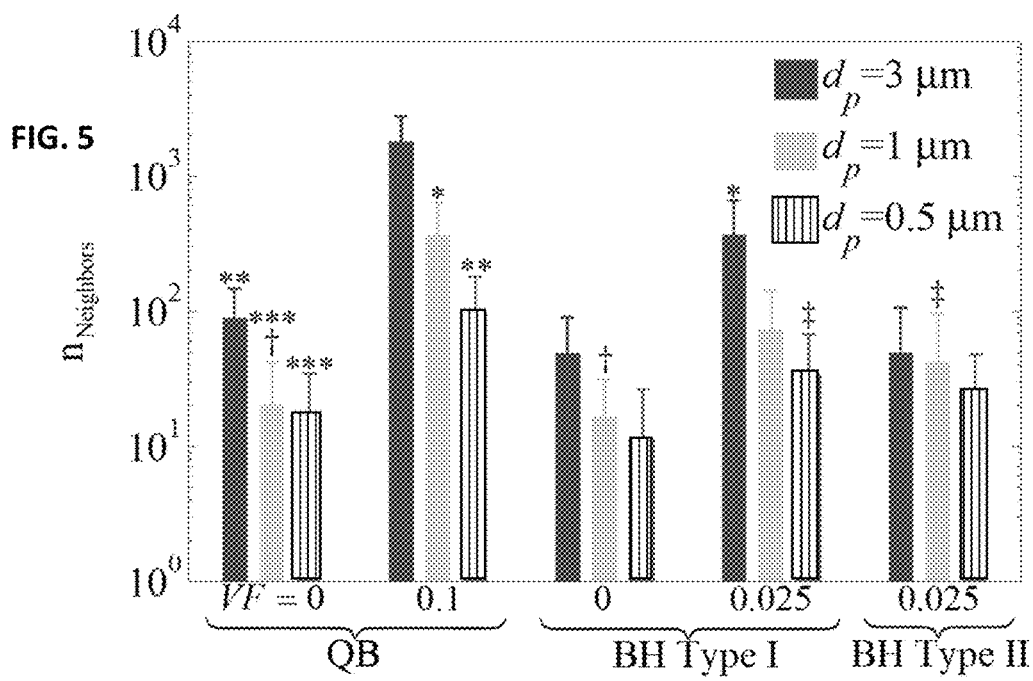
FIG. 5
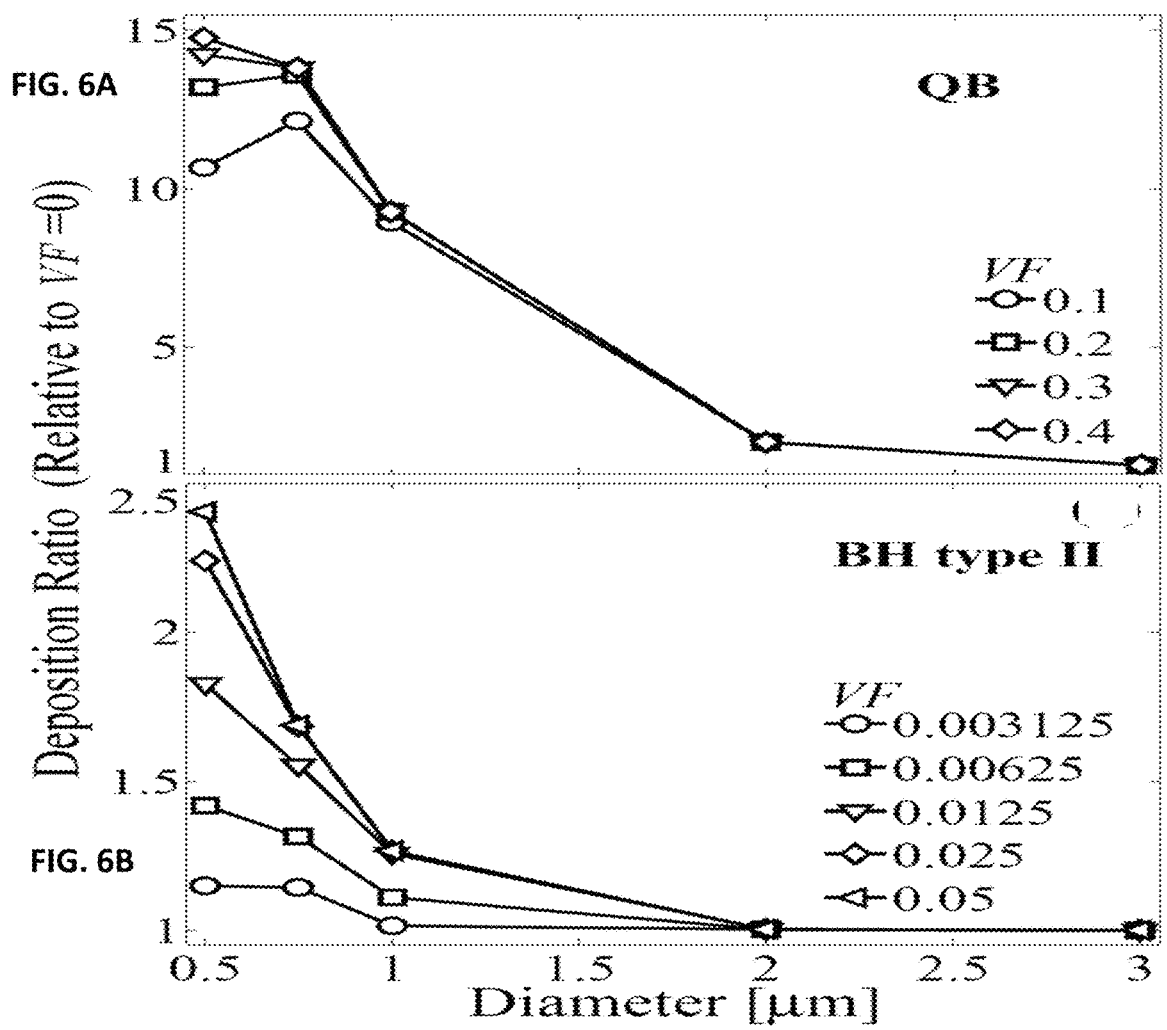
FIG. 6A
FIG. 6B

TARGETED DELIVERY OF AEROSOLS OF MAGNETIZED ACTIVE AGENTS

CROSS-REFERENCE TO RELATED APPLICATIONS

This application is a divisional of U.S. patent application Ser. No. 16/096,374 filed on Oct. 25, 2018, which is a National Phase of PCT Patent Application No. PCT/IL2017/050472 having International filing date of Apr. 25, 2017, which claims the benefit of priority of U.S. Provisional Patent Application No. 62/327,324 filed on Apr. 25, 2016. The contents of the above applications are all incorporated by reference as if fully set forth herein in their entirety.

FIELD OF INVENTION

The present invention is directed to, inter alia, targeted aerosol delivery of active agents.

BACKGROUND OF THE INVENTION

Figure 1A:
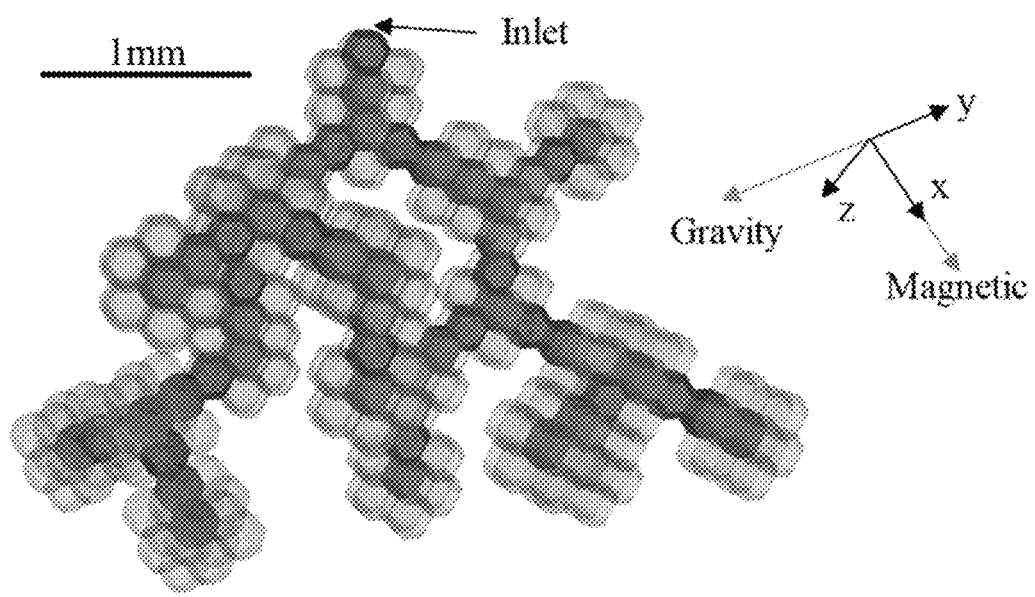

The lungs can be described as a dense tree, where the airways resemble branches, ending with raspberry-like acinar sacs. The acinar sacs are made of alveoli, the basic respiratory units of the lungs. The alveolar lumen is composed of a confluent layer of alveolar epithelial cells where the underlying alveolar wall membrane is perfused by a vast network of capillaries (FIG. 1). The main function of the lungs is undertaken within the alveolar space with the exchange of oxygen and carbon dioxide.

The lungs constitute the largest non-invasive pathway for drug delivery, with an exchange surface estimated at over 100 $m^2$ in an average adult. This pathway is particularly attractive for treating lung diseases topically, including lung cancer, asthma and obstructive diseases (e.g., COPD). Moreover, from a systemic delivery perspective, it can represent the only available non-invasive delivery method for many drugs that cannot be orally administered through the digestive system due to degradation (e.g., proteins such as insulin).

In past decades, there has been substantial progress in understanding respiratory fluid dynamics and the transport of inhaled therapeutic aerosols, including the physical (e.g., aerodynamic) determinants affecting lung deposition outcomes. Nevertheless, the ability to target either a specific pulmonary region (e.g., alveolar region) or a localized point within the airway tree (e.g., lung tumors in the context of bronchogenic carcinoma) remains poor.

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

According to one aspect, the present invention provides a method for depositing a composition to a target site of a subject, the method comprising the steps of:

providing a composition comprising a plurality of particles, each particle comprising a magnetic element; and delivering, via inhalation, an effective amount of the composition to a region of the subject's respiratory tract, wherein the delivering comprises the steps of:

providing a predefined volume of the composition, through a flow path, into a respiratory tract of the subject, in a controllable manner; and providing a predefined volume of gas, through a flow path, into the respiratory tract of the subject in a controllable manner, wherein the gas is devoid of the composition; and applying a magnetic field to the target site within the region of the subject's respiratory tract, thereby facilitating deposition of at least a portion of the composition in the target site within the region of the subject's respiratory tract.

In some embodiments, the delivering step further comprises a preliminary step of providing a first predefined volume of gas, through a flow path, into the respiratory tract in a controllable manner.

In some embodiments, the magnetic element constitutes from 0.1% to 100% by volume of the particle. In some embodiments of the method, the magnetic element constitutes from 0.1% to 10% by volume of the particle. In some embodiments, the particle further comprises one or more active agents.

In some embodiments of the method, the particle has a diameter between 50 nanometers and 3 micrometers. In some embodiments of the method, the particle has a diameter between 50 nanometers and 750 nanometers.

In some embodiments, the invention provides a method for depositing a composition to a target site of a subject, the method comprising the steps of:

providing a composition comprising a plurality of particles, each particle comprising:
a magnetic element; and
one or more active agents,
wherein the magnetic element constitutes from 0.1% to 10% by volume of the particle, and wherein the particle has a diameter between 50 nanometers and 750 nanometers;

delivering, via inhalation, an effective amount of the composition to the subject; and applying a magnetic field to the target site, thereby facilitating deposition of at least a portion of the composition in the target site.

In some embodiments, the delivering step is to a region of a respiratory tract of the subject.

In some embodiments, the delivering step comprises the steps of:

providing a predefined volume of the composition, through a flow path, into a respiratory tract of the subject, in a controllable manner; and providing a predefined volume of gas, through a flow path, into the respiratory tract of the subject in a controllable manner, wherein the gas is devoid of the composition, thereby delivering the composition to the region of the subject's respiratory tract.

In some embodiments, the delivering step further comprises a preliminary step of providing a first predefined volume of gas, through a flow path, into the respiratory tract in a controllable manner.

In some embodiments of the methods described herein, said providing a predefined volume of gas in controllable manner is monitoring the voluntary breathing of a subject and allowing a pre-determined inhaled volume.

In some embodiments of the methods described herein, the method further comprises an exhalation step.

In some embodiments of the methods described herein, the method further comprises applying a super-positioned magnetic field aligned opposing gravity.

In some embodiments, the portion of the composition deposited in the target site is at least 2 times higher than a portion deposited outside of the target site. In some embodiments, the portion of the composition deposited in the target site is at least 10 times higher than a portion deposited outside of the target site.

Figure 4:
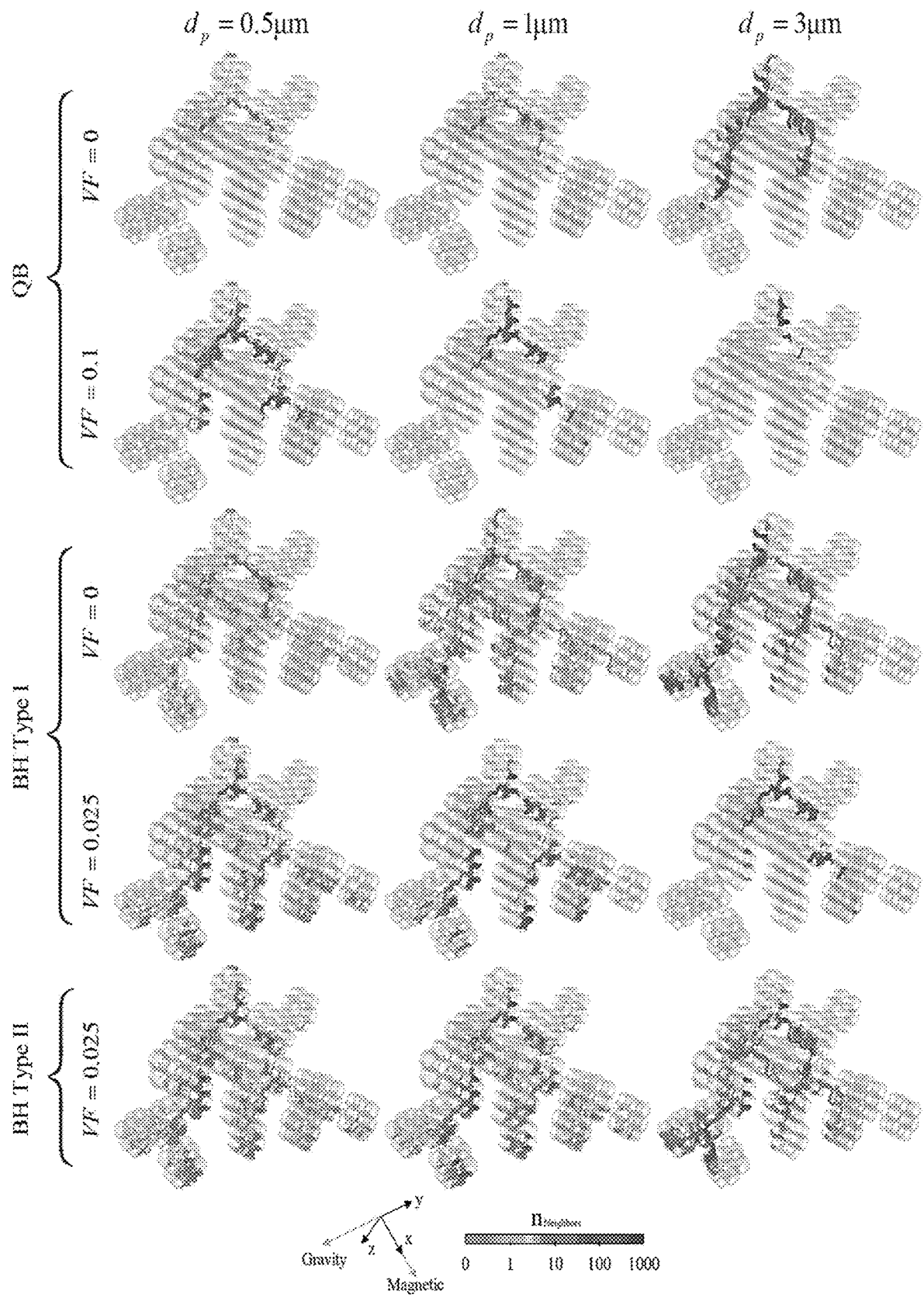

In some embodiments, the magnetic field is applied during a breath-hold. The breath-hold may be applied using a spirometer and a valve (adapted to close after inhaling a pre-determined volume) or by other non-limiting means described herein. In some embodiments, the method of the invention further comprises the step of holding the composition in the region for 0.01 to 10 seconds. In some embodiments, said holding is breath-holding, such as, by the subject.

In some embodiments, the magnetic field has a field strength of 0.1 Tesla to 10 Tesla.

In some embodiments, the method of the invention further comprises the step of stimulating and/or releasing the active agent from the composition being deposited in the target site. In some embodiments, the stimulating and/or releasing is by an external stimulus selected from the group consisting of: magnetic, thermal, ultrasound waves, and radio waves. In some embodiments, the stimulating and/or releasing is performed by applying the external stimulus to a second region of the subject.

According to another aspect, the present invention provides an inhalable particle comprising:

a magnetic element; and one or more active agents, wherein the magnetic element constitutes from 0.01% to 40% by volume of the particle, and wherein the particle has a diameter between 50 nanometers and 750 nanometers.

In some embodiments, the magnetic element constitutes from 0.1% to 10% by volume of the particle. In some embodiments, the magnetic element constitutes from 0.5% to 5% by volume of the particle. In some embodiments, the particle has a diameter between 90 nanometers and 500 nanometers.

In some embodiments, the one or more active agents constitutes from 1% to 10% by volume of the particle. In some embodiments, the one or more active agents are selected from the group consisting of: therapeutic agent, prophylactic agent and diagnostic agent. In some embodiments, the one or more active agents are selected from the group consisting of: a protein, a peptide, a nucleic acid, a small molecule, a lipid, a glycolipid, and an antibody. In some embodiments, the one or more active agents are selected from the group consisting of: a cytotoxic agent, an antineoplastic agent, a chemotherapeutic agent, a radioactive agent, anti-metastatic agent, a hormone, a steroid, a bronchodilator, an anticoagulant, an immunomodulating agent, a P-agonist, an antibiotic, and an antiviral agent.

In some embodiments, the magnetic element of the invention is selected from paramagnetic element or superparamagnetic element. In some embodiments, the magnetic element is selected from the group consisting of: gadolinium, chromium, nickel, copper, iron, or manganese, iron oxides (gamma $Fe_2O_3$, and $Fe_3O_4$), and iron hydroxides $Fe(OH)_2$. In some embodiments, the magnetic element is a superparamagnetic iron oxide nanoparticle (SPION).

According to another aspect, the invention provides a composition comprising a plurality of any of the particles of the invention and a pharmaceutically acceptable carrier. In some embodiments, the composition is formulated for delivery via inhalation.

In some embodiments, the composition is for delivery to the respiratory tract. In some embodiments, the composition is for delivery to the pulmonary system.

In some embodiments, the composition is in a form of an aerosol, wherein the particles are suspended in gas. In some embodiments, the particles within the aerosol are liquid particles. In some embodiments, the particles within the aerosol are solid particles.

According to another aspect, the invention provides a kit comprising:

a composition comprising a plurality of particles, wherein each particle comprises a magnetic element and optionally an active agent; and at least one of the following components:

an inhaler; and a control unit adapted for controlling any one of inhalation time, and inhalation flow rate and inhalation volume.

According to another aspect, the invention provides a kit comprising:

a composition comprising a plurality of particles, wherein each particle comprises:

a magnetic element; and an active agent, wherein the magnetic element constitutes from 0.1% to 5% by volume of the particle, and wherein the particle has a diameter between 50 nanometers and 750 nanometers; and at least one of the following components:

an external magnet which generates a magnetic field; and an inhaler.

In some embodiments, the kit further comprises a control unit for controlling inhalation time, and inhalation flow rate.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1A is a schematic illustration of the acinar domain, showing the alveolar cavities (as light circles) and the acinar ducts (dark circles), the arbitrary gravity and magnetic fields are also shown;

FIG. 1B is a schematic representation of the branching tree;

FIG. 2A is a graph showing "particle magnetization number", which describes the ratio of the magnetic force to the maximal drag force, plotted against a diameter of the particle, for a quiet breathing (QB) maneuver, wherein VF represents the magnetic material volume fraction;

FIG. 2B is a graph showing the magnitude of the magnetic force exerted on the particles corresponding to the particle magnetization number of FIG. 2A;

FIGS. 3A-C show deposition fraction in the acinar model as a function of particle size and different volume fraction (VF) loading of magnetic material, for: QB—Quiet breathing maneuver ($\beta$=0.053, T=3 s) (3A), BH type I—Breath hold maneuver, magnet is constantly on ($\beta$=0.26, T=9.8 s, BH duration=5 s) (3B), BH type II—Breath hold maneuver, magnet is applied only during the breath hold ($\beta$=0.26, T=9.8 s, BH duration=5 s) (3C);

FIG. 4 presents deposition maps shown for different particle diameters (columns), as a function of different magnetic material VF loading (rows). Deposited particles are colored according to the number of neighboring particles located within a 50 μm vicinity (neighbors), the domain inlet is also color-coded highlighting scenarios where particles have exited the domain;

FIG. 5 is a bar graph presenting quantification of particle dispersion in the acinar domain for sample particle sizes as a function of breathing maneuver, mean number of neighboring particles (neighbors) and corresponding error bars (e.g., standard deviation) are shown. Marks ($) and (Q) are the only statistically insignificant pairs, the pairs (*) and () have p<0.05, and (*) marks p<0.01, for all other pairs p<0.001. These values were calculated using a non-parametric Wilcoxon rank sum test;

FIGS. 6A-B are graphs showing ratio of deposited magnetized particles (see legends for VF loading) to deposited non-magnetic particles (VF=0) by utilizing QB—Quiet breathing maneuver (6A), and BH type II—Breath hold maneuver, with magnet applied only during the breath hold (6B).

Figure 7A:
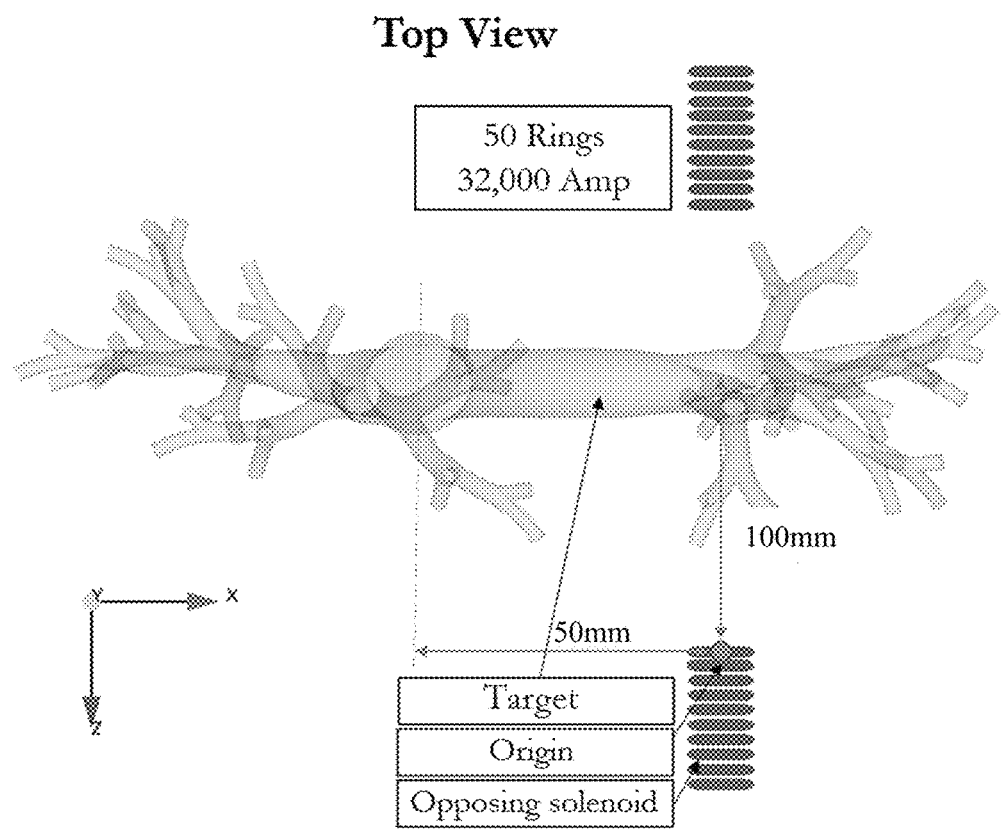
Figures 7B, 7C:
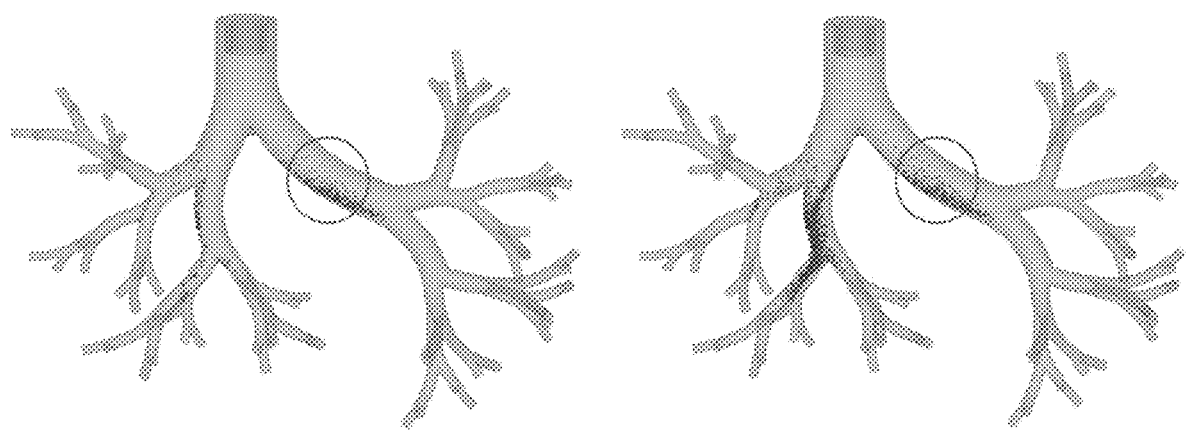

FIGS. 7A-C: Targeted delivery simulations in upper airways. (7A) Clinical setup with two opposing solenoids (not to scale). (7B) Targeted delivery with the present invention magnetic targeting method after breath hold (7B; the targeted region is circled with a solid line) and compared to control (7C).

Figure 8:
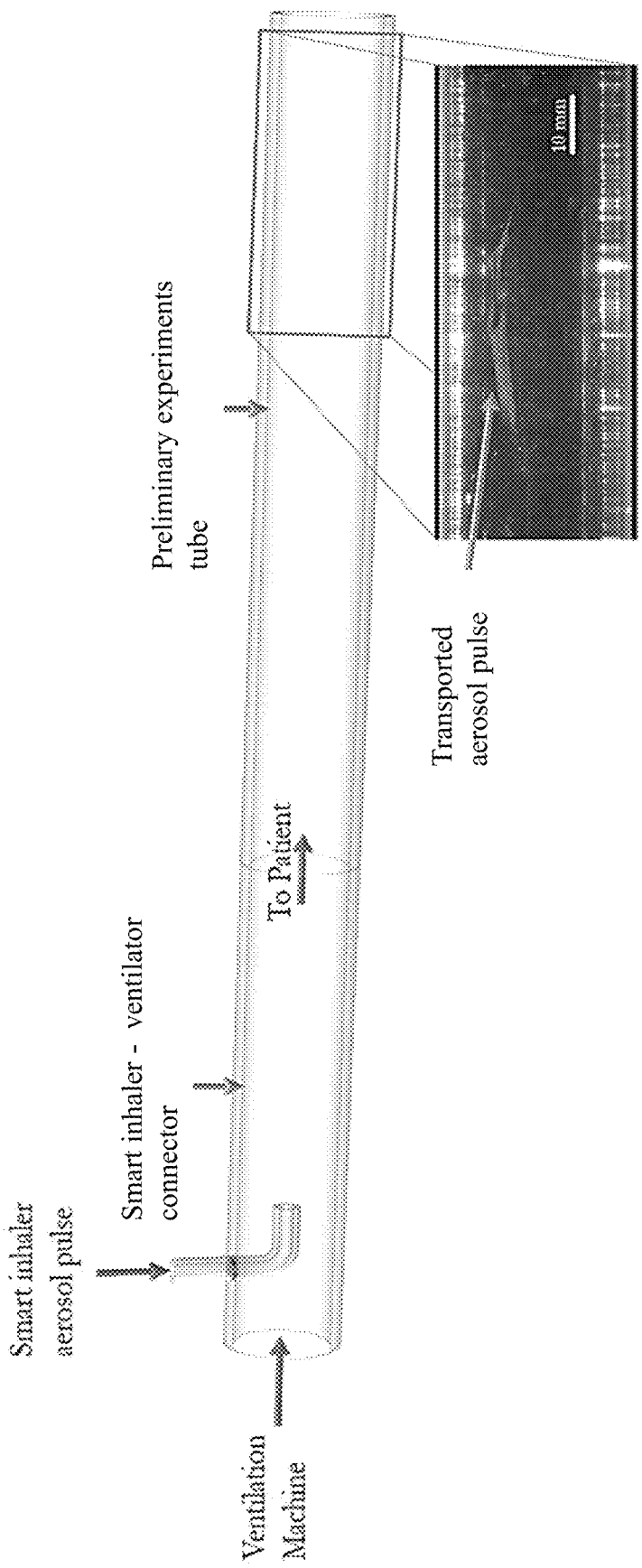

FIG. 8: Aerosol pulse generated using the method and device of the present invention, uniformly transported through a test tube. The spray pulse coming from the smart inhaler is transported by the clean air pushed by the ventilation machine and into the patient's lungs. Inset: instantaneous snapshot of the aerosol bolus taken using planar laser sheet lighting and a high-speed camera (300 Hz).

Figure 9:
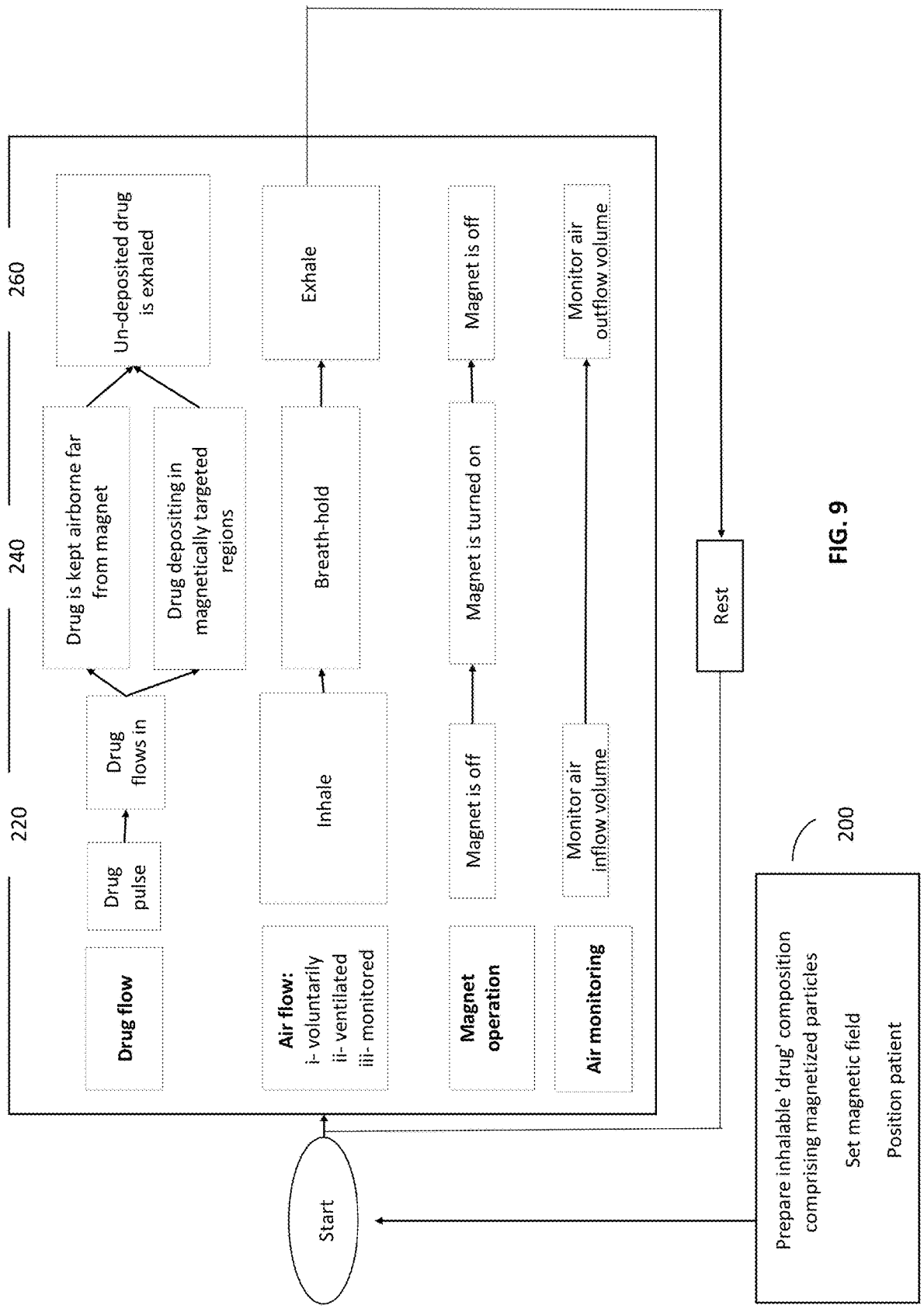

FIG. 9: A flowchart demonstrating the steps for targeting delivery, as a non-limiting example.

DETAILED DESCRIPTION OF THE INVENTION

The present invention provides methods and systems for targeted delivery. In some embodiments, the methods and systems comprise inhalable particles comprising a magnetic element and optionally one or more active agents, administered while utilizing a magnetic field under an inhalation-breathing pattern thereby achieving the targeted delivery.

Advantageously, the particles of the invention may be delivered via inhalation into a predetermined target site of a subject by external guidance which is utilized by an external magnetic field (magnetic targeting). In some embodiments, by positioning a magnetic field across a specific target site (e.g., within the respiratory tract), the increase in deposition by interception allows localization of inhaled magnetized particles (e.g., drug bearing particles) at the target site.

The present invention is based, in part, on the discovery that particles containing magnetic agents and having a diameter in the range of approximately 90-500 nm act as attractive drug carriers or may act as the active agent themselves. Moreover, the compositions and methods described herein enable high deposition fractions while maintaining low volume fraction (VF) of magnetic material for regional targeting of acini or airways; whereas high deposition ratios could be realized in the context of localized point targeting.

Inhalable Particles

In some embodiments, the invention provides one or more inhalable particles (interchangeable 'aerosol particle') comprising a magnetic element. In some embodiments, the particles of the invention are magnetic particles. In some embodiments, the particles of the invention comprise a magnetic element and one or more active agents. In some embodiment, the particle is a liquid particle. Alternatively, the particle is a solid particle.

In one embodiment, the inhalable particle is an agglomerate or droplet comprising a magnetic particle or magnetic element and optionally an active agent (e.g., a drug). It will be understood that the magnetic element and the active agent within the aerosol particles may be of any form or size that is smaller than the aerosol particle. As non-limiting examples, the aerosol particle can be an agglomerate of a mixture of about 50 nm drug particles and about 50 nm magnetic particle; the drug particle can be a particle of about 750 nm coated with about 10 nm magnetic particles; alternatively, the aerosol particle can be a 500 nm droplet in which various size drugs and magnetic particles are suspended.

In some embodiments, the magnetic element and one or more active agents are contained in the particle, without being coupled by a physical adsorption, a chemical bond and/or by a biological interaction. In some embodiments, the particle encapsulates the magnetic element and one or more active agents.

In some embodiments, the magnetic element and one or more active agents are suspended in a carrier, such as a water droplet. Non-limiting suitable carriers are selected from non-toxic, inert liquid filler, diluent, encapsulating material, formulation auxiliary of any type, or simply a sterile aqueous medium, such as saline. In some embodiment, the carrier is selected from an inorganic solvent and an organic solvent. Non-limiting examples of solvents are: ethanol, water, distilled water, and glycerin (glycerol) or mixtures thereof.

The magnetic element and one or more active agents of the particle may be coupled by any coupling technique known to a skilled artisan including but not limited to a physical adsorption, a chemical bond and a biological interaction.

In some embodiments, the one or more active agents are chemically attached (e.g., by a covalent bond) to the magnetic element. Non-limiting examples of covalent bonds include amide, ester, thioester, ether, thioether and disulfide bonds. In some embodiments, the one or more active agents are physically absorbed (e.g., by electrostatic interaction) onto the magnetic element. In some embodiments, the one or more active agents are attached by a biological interaction (e.g., antigen-antibody binding) to the magnetic element.

In some embodiments, the particle has a diameter between 50 nanometers (nm) and 750 nm, 50 nm and 700 nm, 50 nm and 650 nm, 50 nm and 600 nm, 50 nm and 550 nm, 50 nm and 500 nm, 50 nm and 450 nm, 50 nm and 400 nm, 50 nm and 350 nm, 50 nm and 300 nm, 60 nm and 750 nm, 60 nm and 700 nm, 60 nm and 650 nm, 60 nm and 600 nm, 60 nm and 550 nm, 60 nm and 500 nm, 60 nm and 450 nm, 60 nm and 400 nm, 60 nm and 350 nm, 60 nm and 300 nm, 70 nm and 750 nm, 70 nm and 700 nm, 70 nm and 650 nm, 70 nm and 600 nm, 70 nm and 550 nm, 70 nm and 500 nm, 70 nm and 450 nm, 70 nm and 400 nm, 70 nm and 350 nm, 70 nm and 300 nm, 80 nm and 750 nm, 80 nm and 700 nm, 80 nm and 650 nm, 80 nm and 600 nm, 80 nm and 550 nm, 80 nm and 500 nm, 80 nm and 450 nm, 80 nm and 400 nm, 80 nm and 350 nm, 80 nm and 300 nm, 90 nm and 750 nm, 90 nm and 700 nm, 90 nm and 650 nm, 90 nm and 600 nm, 90 nm and 550 nm, 90 nm and 500 nm, 90 nm and 450 nm, 90 nm and 400 nm, 90 nm and 350 nm, 90 nm and 300 nm, 100 nm and 750 nm, 100 nm and 700 nm, 100 nm and 650 nm, 100 nm and 600 nm, 100 nm and 550 nm, 100 nm and 500 nm, 100 nm and 450 nm, 100 nm and 400 nm, 100 nm and 350 nm, 100 nm and 300 nm, 150 nm and 750 nm, 150 nm and 700 nm, 150 nm and 650 nm, 150 nm and 600 nm, 150 nm and 550 nm, 150 nm and 500 nm, 150 nm and 450 nm, 150 nm and 400 nm, 150 nm and 350 nm, or 150 nm and 300. Each possibility represents a separate embodiment of the present invention. In some embodiments, the particle has a diameter between 50 nm to 750 nm. In some embodiments, the particle has a diameter between 50 nm to 500 nm. In some embodiments, the particle has a diameter between 90 nm to 750 nm. In some embodiments, the particle has a diameter between 90 nm to 500.

In some embodiments of the method, the aerosol particle has a diameter of less than 3 micrometers. A skilled artisan will appreciate that particles of larger diameter (e.g., particles of 750 nm to 3 micrometers may be suitable for targeting the upper airways rather than the lower airways, while smaller particles (e.g., less than 1 micrometer) will be suitable for targeting all airway generations.

The term "diameter" refers to the largest linear distance between two points on the surface of the particle. The term "diameter", as used herein, encompasses diameters of spherical particles as well as of non-spherical particles. When referring to multiple particles, the diameter of the particles typically refers to the average diameter of the particles. Particle diameter may be measured using a variety of known techniques including, but not limited to, dynamic light scattering, using and electrostatic classifier, scanning electron microscopy.

As would be understood by a person skilled in the art, the size of the inhalable particle influences the site of deposition in the respiratory tract. ICRP (International Commission on Radiological Protection) guidelines predict deposition fractions as a function of particle diameter across broad lung regions (e.g., extra-thoracic, trachea-bronchial, alveolar), following meta-analysis of empirical data. A skilled artisan will appreciate, that based on ICRP deposition plots, particles having a diameter in the range of 90-500 nm yield the lowest total deposition in the lungs, with less than 10% deposition in the tracheo-bronchial and head airways combined, wherein the un-deposited fractions is subsequently exhaled. These particles are weakly affected by Brownian diffusion and gravity; namely, they act as near tracers of the airflow (i.e., confined to flow streamlines) and are thus essentially washed in and out of the lungs during breathing. As such, this particle size range has often been regarded as a poor choice for inhalation therapy.

The present invention is based, in part, on the unexpected finding that particles having a diameter in the range of approximately 50-500 nm, previously thought to be poor candidate for inhalation therapy, are an advantageous tool for increased regional or point-specific targeting, such as by the use of magnetic force and/or controlled ventilation.

As detailed hereinbelow, aerosol particles of smaller size are more affected by Brownian diffusion, whereas larger particle are subject to gravity forces.

In some embodiments, the aerosol particles of the invention have a diameter of approximately 50-750 nm which is weakly affected by either force (Brownian diffusion and gravity) thereby adhere best to the subjected streamline.

As exemplified in the example section below, deposition of the particle having a size range of 50-750 nm, or more specifically 90-500 nm, in the respiratory tract may be facilitated by a magnetic attraction of the magnetic element to the magnetic force of a magnet. Further, particles having a size range of 50-750 nm, or more specifically 90-500 nm, in combination with non-invasive magnetic forcing, can be leveraged for targeted deposition to the acinar region. Optionally, to achieve targeted deposition, particles may be inhaled through a deep inhalation followed by the onset of a breath hold (BH) maneuver. During the BH maneuver, the acinar region constitutes about 95% of lung volume. At this point, such aerosols (having a diameter range of 90-500 nm or smaller) haven't yet deposited and remain airborne. Following activation of the magnetic field, the particles are forced to rapidly deposit thereby a vast majority (~90%) of inhaled particles are hence anticipated to deposit in the acinar region.

In some embodiments, the one or more active agents constitutes from 0.1% to 99%, 0.1% to 90%, 0.1% to 80%, 0.1% to 70, 0.1% to 60%, 0.1% to 50%, 0.1% to 40%, 0.1% to 30%, 0.1% to 20%, 0.1% to 10%, 0.1% to 5%, 1% to 99%, 1% to 90%, 1% to 80%, 1% to 70, 1% to 60%, 1% to 50%, 1% to 40%, 1% to 30%, 1% to 20%, 1% to 10%, 1% to 5%, 5% to 99%, 5% to 90%, 5% to 80%, 5% to 70, 5% to 60%, 5% to 50%, 5% to 40%, 5% to 30%, 5% to 20%, or 5% to 10% by volume of said particle. In some embodiments, the one or more active agents constitutes from 1% to 10% by volume of said particle.

In some embodiments, the magnetic element constitutes from 0.001% to 40%, 0.005% to 40%, 0.01% to 40%, 0.05% to 40%, 0.1% to 40%, 0.5% to 40%, 1% to 40%, 0.001% to 40%, 0.005% to 40%, 0.01% to 40%, 0.05% to 40%, 0.1% to 40%, 0.5% to 40%, 1% to 40%, 0.001% to 30%, 0.005% to 30%, 0.01% to 30%, 0.05% to 30%, 0.1% to 30%, 0.5% to 30%, 1% to 30%, 0.001% to 20%, 0.005% to 20%, 0.01% to 20%, 0.05% to 20%, 0.1% to 20%, 0.5% to 20%, 1% to 20%, 0.001% to 10%, 0.005% to 10%, 0.01% to 10%, 0.05% to 10%, 0.1% to 10%, 0.5% to 10%, 1% to 10%, 0.001% to 5%, 0.005% to 5%, 0.01% to 5%, 0.05% to 5%, 0.1% to 5%, 0.5% to 5%, or 1% to 5% by volume of the particle. Each possibility represents a separate embodiment of the present invention.

In some embodiments, the magnetic element act also as the active agent. According to such embodiment, the magnetic element constitutes from 0.1% to 100% by volume of the particle. In some embodiments, the magnetic element constitutes from 0.1% to 50% % by volume of the particle. In some embodiments, the magnetic element constitutes from 0.01% to 40% by volume of the particle. In some embodiments, the magnetic element constitutes from 0.5% to 5% by volume of the particle.

Inhalable Compositions

According to some aspects, a composition is provided, the composition comprising a plurality of the particles of the invention and a pharmaceutically acceptable carrier. In some embodiments, the composition is formulated for delivery via inhalation. In some embodiments, the composition is for delivery to the respiratory tract. In some embodiments, the composition is for delivery to the pulmonary system. In some embodiments, the composition is in a form of an aerosol, in which the particles are suspended in gas. In some embodiments, the particles within the aerosol are liquid particles. In some embodiments, the particles within the aerosol are solid particles.

In some embodiments, the composition is an inhalable composition. As used herein the term "inhalable" such as "inhalable particle" or "inhalable composition" refers to certain particles and pharmaceutical compositions of the present invention that are formulated for direct delivery to the respiratory tract during routine or assisted respiration (e.g., by intratracheobronchial, pulmonary, and/or nasal administration), including, but not limited to, atomized, nebulized, dry powder and/or aerosolized formulations. As used herein the term "aerosol" refers to a suspension of solid or liquid particles in a gas.

The term "pharmaceutically acceptable carrier" refers to a carrier that may be taken into the lungs with no significant adverse toxicological effects on the lungs. Numerically the amount may be from about 0.01% of weight to about 99.99% of weight, depending on the activity of the drug being employed.

Such pharmaceutically acceptable carriers may be one or a combination of two or more pharmaceutical excipients. Non-limiting examples of pharmaceutical excipients that are useful as carriers in this invention include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Such pharmaceutically acceptable carriers may include one or more of: solvents, additives, excipients, dispersion media, solubilizing agents, coatings, preservatives, isotonic and absorption delaying agents, surfactants, propellants and the like that are physiologically compatible.

A surfactant can be added to an inhalable pharmaceutical composition of the present invention to lower the surface and interfacial tension between the medicaments and the propellant. Where the medicaments, propellant and excipient are to form a suspension, a surfactant may or may not be required. Where the medicaments, propellant and excipient are to form a solution, a surfactant may or may not be necessary, depending in part, on the solubility of the particular medicament and excipient. The surfactant may be any suitable, non-toxic compound which is non-reactive with the medicament and which substantially reduces the surface tension between the medicament, the excipient and the propellant and/or acts as a valve lubricant.

Examples of suitable excipients include, but are not limited to: lactose, starch, propylene glycol diesters of medium chain fatty acids; triglyceride esters of medium chain fatty acids, short chains, or long chains, or any combination thereof, perfluorodimethylcyclobutane; perfluorocyclobutane; polyethylene glycol; menthol; lauroglycol; diethyl ene glycol monoethyl ether; polyglycolized glycerides of medium chain fatty acids; alcohols; eucalyptus oil; short chain fatty acids; and combinations thereof.

Examples of suitable surfactants include, but are not limited to: oleic acid; sorbitan trioleate; cetyl pyridinium chloride; soya lecithin; polyoxyethylene(20) sorbitan monolaurate; polyoxyethylene (10) stearyl ether; polyoxyethylene (2) oleyl ether; polyoxypropylene-polyoxyethylene ethylene diamine block copolymers; polyoxyethylene(20) sorbitan monostearate; polyoxyethylene(20) sorbitan monooleate; polyoxypropylene-polyoxyethylene block copolymers; castor oil ethoxylate; and combinations thereof. More specific surfactants that may be utilized in the inhalable compositions of this invention are: oleic acid available under the trade name oleic acid NF6321 (from Henkel Corp. Emery Group, Cincinnati, Ohio); cetylpyridinium chloride (from Arrow Chemical, Inc. Westwood, N.J.); soya lecithin available under the trade name Epikuron 200 (from Lucas Meyer Decatur, 111); polyoxyethylene(20) sorbitan monolaurate available under the trade name Tween 20 (from ICI Specialty Chemicals, Wilmington, Del.); polyoxyethylene(20) sorbitan monostearate available under the trade name Tween 60 (from ICI); polyoxyethylene(20) sorbitan monooleate available under the trade name Tween 80 (from ICI); polyoxyethylene (10) stearyl ether available under the trade name Brij 76 (from ICI); polyoxyethylene (2) oleyl ether available under the trade name Brij 92 (from ICI); Polyoxyethylene-polyoxypropylene ethylenediamine block copolymer available under the tradename Tetronic 150 RI (from BASF); polyoxypropylene-polyoxyethylene block copolymers available under the trade names Pluronic L-92, Pluronic L-121 end Pluronic F 68 (from BASF); castor oil ethoxylate available under the trade name Alkasurf CO-40 (from Rhone-Poulenc Mississauga Ontario, Canada); and mixtures thereof. These surfactants may be utilized either as the free base, as a salt, or as a clathrate (such as P-1 1 or hexane clathrates), depending upon the stability and solubility of the active compounds in the specific pharmaceutical composition.

The inhalable compositions of this invention, when in liquid form, may be aerosolized and delivered via nebulization. Nebulizers for delivering an aerosolized solution include the AERx® (Aradigm), the Ultravent® (Mallinckrodt), and the Acorn II@ (Marquest Medical Products). In various embodiments, the pharmaceutical compositions of the present invention are formulated for administration by dry powder inhalation and can comprise one or more additional chemicals and entities which facilitate the administration of the active ingredient.

Delivery of dry powder compositions is typically achieved with an inhaler. A wide variety of dry-powder inhalers may be used to administer various dry powder formulations of the pharmaceutical compositions of the present invention. Examples of commercially available dry-powder inhalers include, but are not limited to, Diskus®, Diskhaler®, and Rotahaler® brand inhalers (GlaxoSmithKline, Inc.), the Turbuhaler® brand inhaler (AstraZeneca), the HandiHaler® brande inhaler (Boehringer Ingelheim Pharma KG), and the Aerolizer brand Inhaler® (Novartis).

Alternatively, the dry powder compositions of this invention can be delivered using a pressurized, metered dose inhaler (MDI), e.g., the Ventolin® metered dose inhaler, containing a solution or suspension of a composition of this invention in a pharmaceutically inert liquid propellant, e.g., a chlorofluorocarbon or fluorocarbon.

In some embodiments, the invention provides a composition for use in the treatment of diseases of the respiratory tract. In some embodiments, the diseases of the respiratory tract are inflammatory and/or obstructive diseases of the respiratory tract, for example malignancies of the respiratory tract, such as lung cancer, lung tumors, lung carcinomas, small cell lung carcinomas, throat cancer, bronchial carcinomas, larynx cancer, head/neck tumors, tongue cancer, sarcomas and blastomas in the region or vicinity of the respiratory tract, in particular the lung. In some embodiments, the diseases of the respiratory tract is selected from the group consisting of asthma and COPD (chronic obstructive pulmonary disease), lung emphysema, chronic bronchitis, pneumonia and hereditary diseases, for example mucoviscidosis, human surfactant protein B deficiency and al-antitrypsin deficiency, and for therapy after a lung transplant and for pulmonary vaccination and for anti-infective therapy of the lung. In some embodiments, the invention provides a composition for use in the treatment of inflammation. In some embodiments, the invention provides a composition for use in the treatment of allergies. In some embodiments, the invention provides a composition for use in the treatment of an autoimmune disease. In some embodiments, the invention provides a composition for use in the treatment of inflammation in the lungs. In some embodiments, the invention provides a composition for use in the treatment of cancer. In some embodiments, the invention provides a composition for use in the treatment of lung cancer.

Magnetic Element

The term "magnetic element" refers to magnetically responsive solid phases which are particles or aggregates thereof which contain one or more metals or oxides or hydroxides thereof, that react to magnetic force upon the influence of a magnetic field, preferably resulting in an attraction towards the source of the magnetic field or in acceleration of the particle in a preferred direction of space. The term "magnetic", as used herein refers to temporarily magnetic materials, such as ferromagnetic, ferrimagnetic, paramagnetic and superparamagnetic materials. Suitable materials of the magnetic element include, for example, iron, cobalt or nickel, magnetic iron oxides or hydroxides, such as $Fe_3O_4$, gamma-$Fe_2O_3$, or double oxides or hydroxides of di- or trivalent iron ions with other di- or trivalent metal ions, e.g. $Co^{2+}$, $Mn^{2+}$, $Cu^{2+}$, $Ni^{2+}$, $Cr^{3+}$, $Gd^{3+}$, $Dy^{3+}$ or $Sm^{3+}$, and any mixtures of such oxides or hydroxides. Preparation processes for magnetic particles are described, e.g., in Schwertmann U. and Cornell R. M., Iron Oxides in the Laboratory, VCH Weinheim 1991, in WO 02/000870 and in DE 196 24 426.

As used herein, the term "ferromagnetic" refers to materials having large and positive susceptibility to an external magnetic field. Ferromagnetic materials have some unpaired electrons so their atoms have a net magnetic moment. They exhibit a strong attraction to magnetic fields and are able to retain their magnetic properties for at least a period of time after the external field has been removed. In some embodiments, a ferromagnetic material can include a ferrimagnetic material, which exhibits different hallmarks of ferromagnetic behavior, e.g., spontaneous magnetization, Curie temperatures, hysteresis, and remanence, but is different from ferromagnetism in terms of magnetic ordering. Examples of ferromagnetic (including ferrimagnetic) materials include, but are not limited to, iron, nickel and cobalt, magnetite ($Fe_3O_4$), maghemite ($\gamma Fe_2O_3 \backslash Fe_2O_3$), jacobsite ($MnFe_2O_4$), trevorite ($NiFe_2O_4$), magnesioferrite ($MgFe_2O_4$), pyrrhotite ($Fe_7S_5$ and other polytypes), greigite ($Fe_3S_4$), feroxyhyte (FeOOH), awaruite ($Ni_3Fe$), wairauite (CoFe), and any combinations thereof.

As used herein, the term "paramagnetic" refers to materials having a small and positive susceptibility to magnetic fields, which are slightly attracted by a magnetic field. In some embodiments, paramagnetic materials do not retain magnetic properties when the external field is removed. These paramagnetic properties are due to the presence of some unpaired electrons and the realignment of the electron orbits caused by the external magnetic field. Examples of paramagnetic materials include, but are not limited to, magnesium, molybdenum, and lithium. The term "superparamagnetic" as used herein refers to the property of materials, which have no permanent (equiaxed) alignment of the elementary magnetic dipoles in the absence of the action of external magnetic fields. In the presence of an external magnetic field, however, superparamagnetic materials can have magnetic susceptibilities at a level similar to ferromagnetic materials. Superparamagnetism can occur when the diameter of the crystalline regions in a normally ferromagnetic substance falls below a particular critical value.

In some embodiments, the magnetic element may be made of a single magnetic material. Alternatively, the magnetic element may be made of a magnetic alloy. In some embodiments, the magnetic element is selected from: paramagnetic element and superparamagnetic element. In some embodiments, the magnetic element is selected from the group consisting of: gadolinium, chromium, nickel, copper, iron, or manganese, iron oxides (gamma $Fe_2O_3$, and $Fe_3O_4$), and iron hydroxides $Fe(OH)_2$. In some embodiments, the magnetic element is a superparamagnetic iron oxide nanoparticle (SPION).

In some embodiments, the magnetic elements are biocompatible. The term "biocompatible", as used herein, is intended to describe materials that induce no systemic toxic side effects in the organism to which they are administered. The magnetic elements of the present invention may be in non-coated or coated form. If the magnetic particles are present in coated form, the coating may be selected from positively or negatively charged electrolytes, such as phosphates, citrates or amines, with silanes, fatty acids or polymers, e.g. polysaccharides, proteins or natural or synthetic polymers. Such a coating of the magnetic particles serves, for example, for reduction of any toxicity of the magnetic particles, for coupling of the pharmaceutical active agent(s) to the magnetic particles, for improving/increasing the passage (of the active agent, optionally together with the magnetic particle(s)) through membranes, etc. Examples of such coatings are described, inter alia, in U.S. Pat. Nos. 4,554,088, 4,554,089, 4,208,294, 4,101,435 and DE 196 24 426. These coatings and the compounds used for them can have reactive functional groups as described in the following. However, these reactive functional groups can also be introduced as required by conventional chemical modifications after the coating operation. Such functional groups can have cation exchange properties, such as, for example, xanthate, xanthide, dicarboxyl, carboxymethyl, sulfonate, sulfate, triacetate, phosphonate, phosphate, citrate, tartrate, carboxylate or lactate groups of natural or synthetic polymers, such as polysaccharides, polyvinyl alcohol (PVA), polyvinylpyrrolidone (PVP) or polyethylene glycol (PEG). These functional groups can be incorporated e.g. into the natural or synthetic polymers described above before or after the coating of the magnetic particles.

Active Agents

In some embodiments, the one or more active agents are selected from the group consisting of: therapeutics, vitamins, electrolytes, amino acids, peptides, polypeptides, proteins, carbohydrates, lipids, polysaccharides, nucleic acids, nucleotides, polynucleotides, glycoproteins, lipoproteins, glycolipids, glycosaminoglycans, proteoglycans, growth factors, differentiation factors, hormones, neurotransmitters, prostaglandins, immunoglobulins, cytokines, and antibodies. Various combinations of these molecules may be used. In some embodiments, the one or more active agents are selected from the group consisting of: a protein, a peptide, a nucleic acid, a small molecule, a lipid, a glycolipid, and an antibody.

In some embodiments, the one or more active agents are selected from the group consisting of: therapeutic agent, prophylactic agent and diagnostic agent. In some embodiments, the one or more active agents are selected from the group consisting of: a cytotoxic agent, an antineoplastic agent, a chemotherapeutic agent, anti-metastatic agent, a hormone, a steroid, a bronchodilator, an anticoagulant, an immunomodulating agent, a P-agonist, an antibiotic, an antifungal agent, and an antiviral agent.

In some embodiments, the one or more active agents are antimicrobial agents. An "antimicrobial agent" in this context can be an antibiotic agent, an antiviral agent (e.g., zanamivir, and oseltamivir) or an antifungal agent (e.g., Amphotericin B, pentamidine), depending on the source of infection in a subject's body.

In some embodiments, the one or more active agents are antibiotics. Non-limiting examples of antibiotics include: cefinetazole; cefazolin; cephalexin; cefoxitin; cephacetrile; cephaloglycin; cephaloridine; cephalosporins, such as cephalosporin C; cephalotin; cephamycins, such as cephamycin A, cephamycin B, and cephamycin C; cepharin; cephradine; ampicillin; amoxicillin; hetacillin; carfecillin; carindacillin; carbenicillin; amylpenicillin; azidocillin; benzylpenicillin; clometocillin; cloxacillin; cyclacillin; methicillin; nafcillin; 2-pentenylpenicillin; penicillins, such as penicillin N, penicillin O, penicillin S, penicillin V; chlorobutin penicillin; dicloxacillin; diphenicillin; heptylpenicillin; and metampicillin.

In some embodiments, the one or more active agents are antihistamines. Non-limiting examples of antihistamines include: azatadine, brompheniramine, chlorpheniramine, clemastine, cyproheptadine, dexmedetomidine, diphenhydramine, doxylamine, hydroxyzine, cetrizine, fexofenadine, loratidine, and promethazine).

In some embodiments, the one or more active agents are chemotherapeutic agents. Non-limiting examples of chemotherapeutic agents include: Actinomycin, Trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine.

In some embodiments, the one or more active agents are antidiabetic agents. Non-limiting examples of antidiabetic agents include alpha-glucosidase inhibitors, amylin analogs, dipeptidyl peptidase 4 inhibitors, incretin mimetics, insulin, meglitinides, non-sulfonylureas, SGLT-2 inhibitors, sulfonylureas, and thiazolidinediones.

In some embodiment, the active agent is a diagnostic agent. For a non-limiting example, the diagnostic agent can be a contrast medium, including e.g. iodine-containing (water-soluble) x-ray-positive contrast media; iodine-containing (water-insoluble) x-ray-positive contrast media; barium containing (water-insoluble) x-ray-positive contrast media; x-ray-negative contrast media; gadolinium compounds, such as e.g. gadolinium DTPA; technetium compounds, such as e.g. compounds containing technetium-99m, for example phosphonates labelled with technetium-99m, Tc-99m-MDP=Tc-99m-methylene-diphosphonate, Tc-99m-tetrofosmin; superparamagnetic iron oxide particles as described above; contrast media which can pass through membranes; enzyme-specific NMR probes, e.g. with paramagnetic dinuclear complexes with lanthanoid ions based on cyclic polyaminopolyacetic acids; glucose contrast media, for example for use in PET (positron emission tomography), including e.g. glucose contrast media coupled to a labelled substance which renders possible external location, e.g. using isotopes which emit positrons, e.g. 18-fluorine, such as, for example, fluoro-2-deoxy-2-D-glucose labelled with 18-fluorine (18FDG), etc. The diagnostic agent can furthermore comprise peptides, proteins, nucleic acids, antibodies, in particular detectable antibodies, low molecular weight detectable compounds, etc.

In some embodiments, the particles may be radioactive particles, such as for targeted deep lung brachytherapy for treatment of lung cancer. The radioactive particles may be administered alone or combined with chemotherapy.

In some embodiments, the active agent is the magnetic element. For a non-limiting example, the inhaled magnetic element may be used in administration of hyperthermia therapy. As used herein "hyperthermia" refers to an induced localized heating at an in vivo site. For example, magnetic nanoparticles can be used to mediate hyperthermia by application of an alternating current field. Conventional alternating current field-based devices such as rotating magnetic field, RF heating, inductive heating, microwave-based procedures, low-field MRI and ultrasound may be used to induce hyperthermia.

Targeted Delivery

In some aspects, the invention provides a method for depositing a composition to a target site of a subject, the method comprising the steps of: providing any of the compositions of the present invention; delivering, via inhalation, an effective amount of the composition to the subject; and applying a magnetic field to the target site, thereby facilitating deposition of at least a portion of the composition in the target site.

As used herein, the term "effective amount" refers to an amount effective, at dosages and for periods of time necessary, to achieve the desired therapeutic result. It should be understood that the depositing methods of the invention may be repeated until a sufficient or pre-determined dose of the active agent is deposited at the target site.

In some embodiments, the invention provides a method for depositing a composition to a target site of a subject, the method comprising the steps of:

providing a composition comprising a plurality of particles, each particle comprising: a magnetic element;

delivering, via inhalation, an effective amount of said composition to a region of the subject's respiratory tract, wherein the delivering comprises the steps of:

providing a predefined volume of the composition, through a flow path, into a respiratory tract of the subject, in a controllable manner; and
  - providing a predefined volume of gas, through a flow path, into the respiratory tract of the subject in a controllable manner, wherein the gas is devoid of the composition; and
- applying a magnetic field to said target site, thereby facilitating deposition of at least a portion of the composition in said target site within the region.

In some embodiments of the method, the particle further comprises one or more active agents. In some embodiments of the method, the delivering step further comprises a preliminary step of providing a first predefined volume of gas, through a flow path, into said respiratory tract in a controllable manner.

In some embodiments, the invention provides a method for depositing a composition to a target site of a subject, the method comprising the steps of: providing a composition comprising a plurality of particles, each particle comprising: a magnetic element; and one or more active agents, wherein said magnetic element constitutes from 0.1% to 10% by volume of said particle, and wherein said particle has a specific diameter range; delivering, via inhalation, an effective amount of the composition to the subject; and applying a magnetic field to the target site, thereby facilitating deposition of at least a portion of the composition in the target site.

In some embodiments of the methods described herein, the specific diameter range of the particle is between 50 nanometers (nm) and 10 micrometers (μm), 50 nm and 3 μm, 50 nm and 1 μm, 50 nm and 750 nm, 50 nm and 700 nm, 50 nm and 650 nm, 50 nm and 600 nm, 50 nm and 550 nm, 50 nm and 500 nm, 50 nm and 450 nm, 50 nm and 400 nm, 50 nm and 350 nm, 50 nm and 300 nm, 60 nm and 10 μm, 60 nm and 3 μm, 60 nm and 1 μm, 60 nm and 750 nm, 60 nm and 700 nm, 60 nm and 650 nm, 60 nm and 600 nm, 60 nm and 550 nm, 60 nm and 500 nm, 60 nm and 450 nm, 60 nm and 400 nm, 60 nm and 350 nm, 60 nm and 300 nm, 70 nm and 10 μm, 70 nm and 3 μm, 70 nm and 1 μm, 70 nm and 750 nm, 70 nm and 700 nm, 70 nm and 650 nm, 70 nm and 600 nm, 70 nm and 550 nm, 70 nm and 500 nm, 70 nm and 450 nm, 70 nm and 400 nm, 70 nm and 350 nm, 70 nm and 300 nm, 80 nm and 10 μm, 80 nm and 3 μm, 80 nm and 1 μm, 80 nm and 750 nm, 80 nm and 700 nm, 80 nm and 650 nm, 80 nm and 600 nm, 80 nm and 550 nm, 80 nm and 500 nm, 80 nm and 450 nm, 80 nm and 400 nm, 80 nm and 350 nm, 80 nm and 300 nm, 90 nm and 10 μm, 90 nm and 3 μm, 90 nm and 1 μm, 90 nm and 750 nm, 90 nm and 700 nm, 90 nm and 650 nm, 90 nm and 600 nm, 90 nm and 550 nm, 90 nm and 500 nm, 90 nm and 450 nm, 90 nm and 400 nm, 90 nm and 350 nm, 90 nm and 300 nm, 100 nm and 10 μm, 100 nm and 3 μm, 100 nm and 1 μm, 100 nm and 750 nm, 100 nm and 700 nm, 100 nm and 650 nm, 100 nm and 600 nm, 100 nm and 550 nm, 100 nm and 500 nm, 100 nm and 450 nm, 100 nm and 400 nm, 100 nm and 350 nm, 100 nm and 300 nm, 150 nm and 10 μm, 150 nm and 3 μm, 150 nm and 1 μm, 150 nm and 750 nm, 150 nm and 700 nm, 150 nm and 650 nm, 150 nm and 600 nm, 150 nm and 550 nm, 150 nm and 500 nm, 150 nm and 450 nm, 150 nm and 400 nm, 150 nm and 350 nm, 150 nm and 300 nm. Each possibility represents a separate embodiment of the present invention.

In some embodiments, particles having a diameter size larger than 500 nanometers or 750 nanometers ('large particles') may be utilized for the methods of the invention. In some embodiments, large particles, such as having a diameter ranging between 1 μm and 10 μm, may be utilized for the methods of the invention. In some embodiments, large particles may be utilized by applying a superpositioned magnetic field aligned opposing gravity, to eliminate influence of gravitational forces.

In some embodiments, the aerosol particle may be a porous aerosol particle to reduce inertial effects.

In some embodiments, the inhalation is through the mouth, through the nose or through a combination thereof. In some embodiments, the inhalation is an oral inhalation through the mouth. In some embodiments, the inhalation utilizes a nebulizer or an inhaler.

In some embodiments, the delivering is to a region of respiratory tract of the subject. In some embodiments, the region is a region of the lower respiratory tract. Non-limiting examples of regions of the lower respiratory tract include: the portion of the larynx below the vocal cords, trachea, bronchi and bronchioles, alveolar ducts, alveolar sacs, and alveoli. In some embodiments, the region is a region of the lung selected from the group consisting of: respiratory bronchioles, alveolar ducts, alveolar sacs, and alveoli. In some embodiments, the region is one of the lungs, a lobe or several lobes. In some embodiments, the region is selected from the group consisting of: trachea, main bronchus, lobar bronchus, segmental bronchus, conducting bronchiole, terminal bronchiole, respiratory bronchiole, alveolar duct, alveolar sac, and alveoli. In some embodiments, the region is the trachea. In some embodiments, the region is the main bronchus. In some embodiments, the region is the lobar bronchus. In some embodiments, the region is the segmental bronchus. In some embodiments, the region is the conducting bronchiole. In some embodiments, the region is the terminal bronchiole. In some embodiments, the region is the terminal bronchiole. In some embodiments, the region is the terminal bronchiole. In some embodiments, the region is the respiratory bronchiole. In some embodiments, the region is the alveolar duct. In some embodiments, the region is the alveolar sac. In some embodiments, the region is the alveoli. In some embodiments, the region is the alveoli from which the composition reach the pulmonary system through the capillary rich alveolar walls.

In some embodiments, the target site is a specific site within the region. In some embodiments, the target site comprises and/or consists of the entire region (e.g., one or more lobes, alveoli, etc.).

In some embodiments, the applied magnetic field attracts the particles of the invention into the target site. The term "magnetic field" refers to a magnetic field which is generated by a magnet as the source. The magnetic field is capable of attracting the magnetic elements, thereby attracting the particles of the invention, against other physical forces acting on these (e.g., gravity).

In one embodiment, the methods of the invention further comprise applying a first magnetic field for attracting the magnetic elements inhaled by the subject as well as a second magnetic field to act against gravity forces. As a non-limiting option, the first magnetic field may be applied during the breath-hold (BH) whereas the second magnetic field may be applied through the treatment.

In some embodiments, the second magnetic field being applied against (e.g., substantially counter to) gravity (i.e., anti-gravity field), is exerted without the first magnetic field (that attracts the magnetic elements). In some embodiments, the anti-gravity magnetic field is applied throughout the methods described herein. In some embodiments, the anti-gravity magnetic field is applied only during the inhalation, thereby allowing the particles to sediment due to gravity during the breath-hold.

In some embodiments, the magnetic field has a field strength of at least 0.1 Tesla, 0.2 Tesla, 0.5 Tesla, or 1 Tesla. In some embodiments, the magnetic field has a field strength of at most 0.1 Tesla, 0.2 Tesla, 0.5 Tesla, 1 Tesla, 2 Tesla, 5 Tesla, 10 Tesla. Each possibility represents a separate embodiment of the present invention. The different embodiments can be combined at will. In some embodiments, the magnetic field has a field strength of 0.1 Tesla to 10 Tesla.

In some embodiments, the delivering is by quiet breathing (QB). In some embodiments, the delivering is by quiet breathing (QB) and breath hold (BH). As used herein the term "quiet breathing" refers to a normal respiration. The term "breath-hold", as used herein, means that the composition is held in the respiratory tract (e.g., the lung) for a breath-hold time to facilitate deposition of the composition. In some embodiments, the method further comprises the step of holding the composition in the region. In some embodiments, the breath-hold duration is between 0 seconds to 30 seconds, 0.1 seconds to 30 seconds, 0.5 seconds to 30 seconds, 1 second to 30 seconds, 5 seconds to 30 seconds, 0 seconds to 10 seconds, 0.1 seconds to 10 seconds, 0.5 seconds to 10 seconds, 1 second to 10 seconds, 5 seconds to 10 seconds, 0 seconds to 5 seconds, 0.1 seconds to 50 seconds, 0.5 seconds to 5 seconds, 1 second to 5 seconds, 5 seconds to 5 seconds, 0 seconds to 5 seconds, 0.1 seconds to 5 seconds, 0.5 seconds to 5 seconds, 1 second to 5 seconds, 0 seconds to 1 second, 0.1 seconds to 1 second, 0.2 seconds to 1 second, 0.5 seconds to 1 second, 0 second to 0.5 seconds, 0.1 seconds to 0.5 seconds, 0.2 second to 0.5 seconds, or 0.3 seconds to 0.5 seconds. Each possibility represents a separate embodiment of the present invention. The different embodiments can be combined at will.

In some embodiments, the method further comprises the step of holding the composition in the region for 0 to 10 seconds. In some embodiments, the method further comprises the step of holding the composition in said region for 0.1 seconds to 0.5 seconds.

As exemplified in the example section, using a BH maneuver, the amount of magnetic material needed may be reduced. Additionally, in some embodiments, a good dispersion may be achieved if the magnet is turned on only during the BH. In some embodiments the magnet is brought towards the patient only during the BH. In some embodiments the patient approaches towards the magnet only during the BH.

In some embodiments, the composition is delivered by a short pulse followed by inhalation of gas (e.g., air, oxygen, etc.). In some embodiments, in order to deliver the composition to a specific region of the respiratory tract, a predefined volume of gas should be inhaled. In some embodiments, the composition is delivered to a specific region of the respiratory tract monitoring the volume of gas inhaled. In some embodiments, a breath hold is utilized upon delivery of the composition to the region of the respiratory tract to allow deposition of the composition.

In some embodiment, the delivering step utilizes a controlled inhalation.

In some embodiments, the delivering comprises the steps of: providing a predefined volume of said composition, through a flow path, into said respiratory tract of said subject, in a controllable manner; and providing a predefined volume of gas, through a flow path, into said respiratory tract of said subject in a controllable manner, wherein the gas is devoid of said composition, thereby delivering said composition to the region of the subject's respiratory tract. In some embodiments, the delivering step further comprises a preliminary step of providing a first predefined volume of gas, through a flow path, into said respiratory tract in a controllable manner.

In some embodiments, the applied magnetic field is utilized for targeting a portion of the composition to a specific target site within the region of the subject's respiratory tract. "Targeting" as used herein, is intended to encompass both attracting the composition to the target site from a more distal location within the region of the subject's respiratory tract and retaining the composition at the target site. In some embodiments, due to a locally exerted external magnetic field, a portion of the composition is attracted to a specific target site within the region of the subject's respiratory tract. In some embodiments, the portion of the composition attracted to the specific target site is trapped within the target site. In some embodiments, a remaining portion of the composition, which was not trapped within the target site, leaves the patient's respiratory tract during subsequent exhalation.

In some embodiments, the method may be used for targeted delivery of drugs to a specific region of the lungs. For a non-limiting example, Alpha-1 trypsin deficiency treatment drug, which is currently administered by injection, may be delivered using the methods of the invention.

In some embodiments, the method may be used for reducing side effects (e.g., effects associated with upper airway deposition). For a non-limiting example, the method may be used to deliver a drug such as Pentamidine which is intended for the deep respiratory airways and causes severe side effects when depositing in upper-airways.

In some embodiments, the method further comprises the step of stimulating and/or releasing the active agent from the composition deposited in the target site. In some embodiments, stimulating and/or releasing is by an external stimulus selected from the group consisting of: magnetic, thermal, ultrasound waves, and radio waves. In some embodiments, the stimulating and/or releasing is performed by applying said external stimulus to a second region of said subject.

In a non-limiting example, following the deposition of the composition in a first target site, an external stimulus is applied onto a surface of a second target site, thereby activating the active agents of the deposited composition within a portion of the second target site which overlaps with the first target site.

In some embodiments, a magnetically deposited portion of the composition is at least 5, 10, 20, 30, 50 times higher than a portion of the composition deposited in the absence of a magnetic field. In some embodiments, a portion of the composition magnetically deposited within the applied magnetic field is at least 5, 10, 20, 30, 50 times higher than a portion deposited outside the magnetic field.

In some embodiments, the method of the invention is for prophylaxis and/or therapy of diseases of a subject's respiratory tract and/or lungs, inflammatory and/or obstructive diseases of a subject's respiratory tract. In some embodiments, the method of the invention is for prophylaxis and/or therapy of diseases of a subject's respiratory tract and/or lungs selected from: lung cancer, lung tumors, lung carcinomas, small cell lung carcinomas, throat cancer, bronchial carcinomas, larynx cancer, head/neck tumors, tongue cancer, melanomas, sarcomas and blastomas in a region or vicinity of a subject's respiratory tract. In some embodiments, the methods of the invention are for prophylaxis and/or therapy of diseases of a subject's respiratory tract and/or lungs selected from: asthma, COPD (chronic obstructive pulmonary disease), lung emphysema, chronic bronchitis, pneumonia and hereditary diseases, mucoviscidosis, human surfactant protein B deficiency and al-antitrypsin deficiency. In some embodiments, the method of the invention is for therapy after a lung transplant. In some embodiments, the method of the invention is for pulmonary vaccination. In some embodiments, the method of the invention is for anti-infective therapy of a subject's lung.

In some embodiments, the invention provides a method for treating inflammation. In some embodiments, the invention provides a method for treating allergies. In some embodiments, the invention provides a method for treating an autoimmune disease. In some embodiments, the invention provides a method for treating inflammation in the lungs. In some embodiments, the invention provides a method for treating cancer. In some embodiments, the invention provides a method for treating lung cancer.

Magnets

In some embodiments, the system and kits of the invention further comprise a magnet. The term "magnet" refers to any magnet which is suitable to generate the magnetic field described above. For example, permanent magnets or electromagnets (operated by electric current) may be employed in the context of the present invention. The magnetic field may be switched on or off e.g. by mechanical removal or turning away of the poles of the magnet in the case of permanent magnets, or by switching on or off of the electric current required for generation of the magnetic field. The intensity (the field strength of the magnet) is typically controlled via suitable measurement and control instruments connected to the magnet. The magnet may be placed outside the body of the subject onto an external surface of the target site and/or adjacent to the target site. Alternatively, the magnet may be placed adjacent to a tissue and/or organ and/or target site.

In some embodiments, the magnetic field is applied throughout the treatment. For a non-limiting example, the magnetic field may be applied from the delivering step until exhalation following deposition of a portion of the composition. In some embodiments, the magnetic field is applied for a portion of the treatment period. For non-limiting example the magnetic field is applied during a resting phase between inhalation and exhalation.

Controlled Inhalation

In some embodiments, the invention further provides a device for controlling the delivery of any of the compositions of the invention, via inhalation, to specific regions of the respiratory tract. In some embodiments, the device regulates inhalation of gas or air through a flow path into a respiratory tract. In some embodiments, the device is adapted to use the compositions of the invention. In some embodiments, the device is adapted to allow inhalation of particles having a diameter size range between 50 and 750 nm.

In some embodiments, the device comprises a flow rate limiting mechanism to regulate the flow rate of gas (e.g., air) and/or any of the compositions of the invention; and a timer to control inhalation time of the gas and/or any of the compositions of the invention.

In some embodiments, the device comprises a volume limiting mechanism to regulate the total inhaled volume of gas (e.g., air) and/or any of the compositions of the invention. The volume can be up to 3 Liters, preferably 10-500 ml. It should be understood that the volume will depend on the location of the targeted region.

In some embodiments, the device further comprises a control unit. In some embodiments, the control unit regulates an inhalation flow rate through a flow path. In some embodiments, the inhalation rate has a predefined flow rate range between 0.01 L/min and 60 L/min. In some embodiments, the inhalation rate has a predefined flow rate range between 0.1 L/min and 3 L/min.

In some embodiments, a subject may be mechanically ventilated. In some embodiments, the subject may comply with the flow rates defined by the device. In some embodiments, the control unit is adapted to measuring any one of inhalation flow-rate and volume and determining the release of the aerosol magnetic particles (e.g., comprising the drug) at the required time and duration, such as during breath-hold. In one embodiment, the device comprises a spirometer, for determining the inhalation flow-rate and volume, and a control unit for determining the time and duration for applying the aerosol magnetic particles.

In some embodiments, the control unit operates a timer to allow inhalation of gas and/or any of the compositions of the invention for a predefined time period to facilitate inhalation of predefined volume of gas and/or any of the compositions of the invention. For a non-limiting example, control unit initiates the timer for a predefined time period to allow introduction of a predefined volume of gas through a flow path to a respiratory tract, once the subject inhaled the predefined volume of gas, control unit initiates the timer for a second predefined time period to allow introduction of a predefined volume of the composition through the flow path to a specific region of the respiratory tract.

Alternatively, devices for controlling inhalation, which are known in the art, may be utilized for delivery of the inhalable composition of the instant invention to a specific region of the respiratory tract. U.S. Pat. No. 8,534,277 discloses devices and systems for targeting aerosolized particles to a specific area of the lungs, the contents of which is incorporated herein by reference in its entirety. For a non-limiting example, devices such as the devices disclosed in U.S. Pat. No. 8,534,277 may be utilized for delivery of the inhalable composition of the instant invention to a specific region of the respiratory tract.

The controlled inhalation of the present invention may a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Reference is now made to FIG. 9 which is a flowchart of a non-limiting example of the targeting methods described herein. An inhalable composition comprising magnetized particles and a drug is provided (termed under FIG. 9 as 'Drug'), the magnetic field is set and the patient is position (step 200). The targeting methods includes subsequent (e.g., altering) flow of the drug and air, i.e., devoid of the magnetic particles and drug (step 220). For depositing the drug at the requested position, air flow is held (breath-hold), the magnet is turned, and consequently the drug is deposited in the magnetically targeted region (step 240). Thereafter, an exhalation step follows, wherein the magnet is turned off, so as to exhale the un-deposited drug (step 260). The method may be repeated so as to deposit larger amount of the drug at the target region.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Kits

According to some aspects, the invention provides a kit comprising any of the compositions of the invention; and one or more components for the delivery of any of the compositions of the invention, via inhalation, to a region of the respiratory tract and/or for the deposition of the composition in a specific target site within the region of the respiratory.

In some embodiments, the invention provides a kit comprising any of the compositions of the invention; and at least one of the following components: an external magnet which generates a magnetic field; and an inhaler. In some embodiments, the kit further comprises a control unit for controlling at least one of the following parameters: inhalation time, inhalation flow rate, strength of applied magnetic field, duration of applied magnetic field, and timing of applied magnetic field. In some embodiments, the control unit is for controlling inhalation time, and inhalation flow rate. In some embodiments, the control unit controls one or more inhalation parameters consisting of: beginning of aerosol administration time, duration of aerosol administration time, volume of gas (e.g., clean air inhaled) introduced prior and/or post aerosol inhalation, and breath hold duration.

In some embodiments, controlling the inhalation time and/or inhalation flow rate may be facilitated by controlling the operation of the nebulizer and/or the inhaler.

Control of the magnetic field may be facilitated by controlling an operation of the magnet, for example, by an electric circuit which triggers a signal in the nebulizer or inhaler at the start and end of the inhalation or exhalation of the patient, by which in turn the magnetic field of a magnet as described here is switched on or off.

In some embodiments, the kit comprises: a composition comprising a plurality of particles, wherein each particle comprises: a magnetic element; and an active agent, wherein said magnetic element constitutes from 0.1% to 10% by volume of said particle, and wherein said particle has a diameter between 50 nanometers and 750 nanometers; and at least one of the following components: an external magnet which generates a magnetic field; and an inhaler. In some embodiments, the kit further comprises a control unit.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise", "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Various embodiments and aspects of the present invention as delineated hereinabove and as claimed in the claims section below find experimental support in the following examples. Reference is now made to the following examples, which together with the above descriptions illustrate some embodiments of the invention in a non-limiting fashion.

Example 1

Materials and Methods
Acinar Domain and Breathing Motion

Figure 1B:
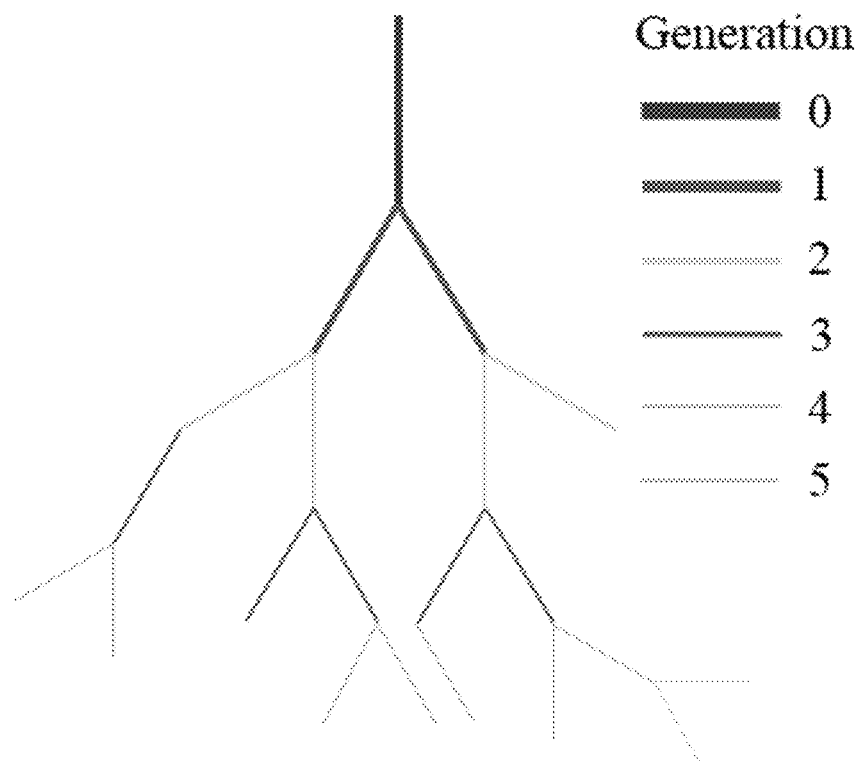

Past morphometric studies have broadly described the underlying alveolar structure as constructed of polyhedral shapes with a single flat inter-alveolar septa separating adjacent airspaces. This morphology can be well described by space-filling octahedral shapes assembled into honeycomb-like structures. In accordance with recent computational fluid dynamics (CFD) studies, an acinar tree consisting of repeating polyhedral units was constructed (FIG. 1A), with up to six asymmetrically branching generations (FIG. 1b). The tree extends on the scale of a few millimeters and consists of 343 polyhedra, of which 277 represent alveolar cavities, while the rest constitutes the acinar ducts (e.g., the skeleton of the tree).

While breathing motion is known to be asynchronous and spatially heterogeneous, the principle mode remains nevertheless self-similar. Hence, breathing was modeled by kinematically expanding and contracting the acinar domain using a sinusoidal function:

$$x(t) = x_0\left[1 + \frac{\beta}{2} + \frac{\beta}{2}\sin\left(\frac{2\pi t}{T} + \frac{\pi}{2}\right)\right], \quad \text{Equation No. 1}$$

where X, $X_0$ are respectively the current and initial positions of each point on the wall, t is the time, β is the linear expansion factor (depending on the tidal breathing volume) and T is the breathing period. Depending on the breathing maneuver simulated (see Examples below), the parameters R and T were modulated for an average human adult.

Fluid and Particle Transport Equations

Air inhaled into the acinus is assumed to be incompressible, Newtonian, and isothermal. The transient motion of air is governed by the continuity and Navier-Stokes equations adapted for volume changes over the breathing cycle. The respiratory oscillatory flow is mainly governed by two non-dimensional numbers, the Womersley and Reynolds numbers. The peak Reynolds number in the presented domain reaches up to Re=$v_f$*d/$v_f$≤0.3 near the inlet (here, d represents the acinar diameter, $v_f$ is the fluid velocity and or is the kinematic viscosity), and drops down orders of magnitude with increasing distal generation. Correspondingly, the Womersley number, defined as Wo=d*(ω/$v_f$)0.5 (where ω=2π/T is the angular breathing frequency), represents the ratio between oscillatory inertia and viscous forces, and remains Wo<0.1 everywhere in the domain. Hence, the flow velocity is in phase with the pressure gradient and the flow behaves as quasi-steady. These numbers agree well with previously published data.

For the boundary conditions, a no-slip condition is implemented on the domain walls, and an arbitrary zero pressure condition on the inlet. For the inhaled aerosols, a Lagrangian framework governed by the force balance is implemented in the absence of electrostatic, hygroscopic and other forces:

$$m_p \frac{dv_p}{dt} = F_{gravity} + F_{drag} + F_{Brownian} + F_{magnetic}, \quad \text{Equation No. 2}$$

Here, $m_p$ is the particle mass and $v_p$ is the particle velocity. The gravitational force ($F_{gravity}$) acts in the $-y$ direction (see FIG. 1A) and the drag force ($F_{drag}$) is modeled by Stokes' drag law incorporating the Cunningham correction factor for air as the carrier fluid. The Brownian force which accounts for the stochastic motion of diffusive particles is given by:

$$F_{Brownian} = m_p G_i \sqrt{\frac{\pi S_0}{\Delta t}}. \quad \text{Equation No. 3}$$

Here, $G_i$ is a random vector with its components following a Gaussian distribution with zero mean and unit variance. $\Delta t$ is the Brownian force time step and $S_0$ is the spectral intensity, given by:

$$S_0 = \frac{216 k_B T_f \mu_f}{\pi^2 d_p^5 C_c \rho_p^2}, \quad \text{Equation No. 4}$$

Where $k_B$ is the Boltzmann constant, $\mu_f$ is the viscosity and subscript f represents the fluid phase, $T_f=311$ K is the body temperature, $d_p$ is the particle diameter, C, is the Cunningham correction Equation No. 5:
factor and $\rho_p$ is the particle density. Finally, the magnetic force acting on a particle is given by:

$$F_{magnetic} = \begin{cases} \frac{\pi d_p^3}{6} \cdot VF \cdot \mu_0 \frac{\chi_p}{2} \cdot H \nabla H & H < M_{sat}/\chi_p \\ \frac{\pi d_p^3}{6} \cdot VF \cdot \mu_0 M_{sat} \hat{H} \nabla H & H \geq M_{sat}/\chi_p \end{cases},$$

where VF is the magnetic material volume fraction, $\chi_p$ is the magnetic susceptibility, $\mu_0$ is the permeability of free space, $M_{sat}$ is the magnetic material saturation, and H is the magnetic field strength, with $\hat{H}$ being its unit direction vector.

Particles enter the acinar domain through the inlet after 150 ml of air is inhaled into the lungs (representing about 5% increase in volume relative to the baseline functional residual capacity, FRC). This initial delay until injection represents the volume inhaled before particles have passed through the dead space (e.g., conducting airways) and reach the acinar region. Once injected into the acinar domain, particles touching the wall are assumed to have deposited and cannot bounce back. Alternatively, particles that get exhaled through the domain exit (entrance) are not inhaled back during the following cycle.

Magnetic Particles

Following the work of Dames et al, water droplets ($\rho_p=1000$ kg/m$^3$) were used as the inhaled (carrier) particles in our simulations. In an attempt to generalize the results presented, five distinct particle diameters were examined (0.5, 0.75, 1, 2 and 3 μm). For each size, up to 10 different magnetic material VFs were considered (ranging from 0 to 40% v/v), yielding a total of 50 different examined particle types in each simulation; note that the density of the resulting SPION-loaded particles are adjusted according to VF. The magnetic material loaded into the particles was magnetite ($Fe_3O_4$) (super magnetic iron oxide nanoparticles). These SPIONs have a mass density of $\rho_{magnetic}=5175$ kg/m$^3$, a magnetic susceptibility of $\chi=20$, and a magnetic material saturation of $M_{sat}=4.48 \cdot 10^5$ A/m. To externally manipulate the deposition of the particles, a realistic unidirectional magnetic field (see FIG. 1a for field orientation) of strength $H_x=3.4 \cdot 10^5$ A/m with a gradient $dH_x/dx=5.5 \cdot 10^6$ A/m$^2$ was exerted. Substituting these values back into Eq. (5), it can be sees that under such realistic conditions the particles are always magnetically saturated. Note that given the relatively small dimensions of the acinar domain investigated (~1 mm), the selected magnetic field properties are assumed to be locally constant and unidirectional.

Numerical Methods

The acinar domain was meshed with tetrahedral cells using Ansys Gambit and refined in regions of high velocity gradients (e.g., near the inlet). The fluid motion was simulated using Ansys Fluent Finite volume solver, where a dynamic mesh function was implemented to expand and contract the domain. Rigorous convergence tests were performed to ensure that all numerical errors remained sufficiently low. Namely, mesh density, order and type of numerical models, time step and residual numerical errors were all examined. As a result, a mesh of about 3 million cells was eventually selected, with a $10^{-3}$ seconds (s) time step. Moreover, the inventors have made use of a coupled pressure-velocity coupling scheme, a Green-Gauss node based for gradients, a body-force weighted for pressure, a 3$^{rd}$ order MUSCUL for momentum and 2$^{nd}$ order for the transient formulation.

To simulate the motion of particles, an in-house DEM (discrete element method) solver was written and one-way coupled to the fluid. The particles were temporally integrated using an explicit 1$^{st}$ order Euler model. Thorough convergence tests were performed on the DEM solver, after which a time step of $2 \cdot 10^{-7}$ s was selected and 10,000 particles were used for each particle type to ensure good deposition statistics. It is important to note here that the time step implemented for the Brownian force, e.g., Equation No. 3, was tuned independently of the fluid's and particles' time steps, by using the expected root-mean square (RMS) velocity of the short time scales. As a result, the magnitude (and direction) of this force changes only once in two particle time steps. Particles were randomly injected from the domain inlet with parabolic weighting towards the inlet center and a uniform temporal distribution (until the end of inhalation). Finally, the inventor's DEM code was compared and validated according to established analytical models.

Inhalation Maneuvers

The feasibility of controlling particle deposition using SPIONs is first examined with a quiet breathing (QB) maneuver. In this simulation, $\theta=0.053$ (representing a 16.8% expansion in lung volume about FRC) and the breathing period (T) is 3 seconds. As mentioned above, particles are injected after crossing the dead space; this corresponds here to approximately 0.6 s, e.g., t/T=0.2 and the injection continues until exhalation (t/T=0.5).

In a following step, a breathing maneuver more common to drug administration is examined, such as a deep breath followed by a breath hold (BH). This maneuver was tested for two different magnet operation scenarios. In the first, the magnet is constantly on during the drug administration (breath-hold type I—BH1). In the second scenario, the magnet is on only during the BH (breath-hold type II—BH2). In these two BH cases, T=9.8 s and 3=0.26, representing a deep breath with 100% lung volume expansion. Note here that the breathing cycle is divided into three parts, e.g., the inhalation, which lasts for 2.4 s, a subsequent BH lasting 5 s, and finally a 2.4 s exhalation. In such cases, the non-dimensional numbers (Re and Wo) remain on the same order of magnitude as in QB. As a result of the large volume expansion, flow rates are higher for the BH cases; for such cases particles are accordingly injected at 0.41 s.

Non-Dimensional Overview

For the range of particle sizes examined, the strongest force exerted on the droplets during inhalation remains viscous drag. In the absence of the magnetic force, low flow velocities around the time of flow reversal (t/T~0.5) allow either gravity or diffusion to become dominant for the largest Equation No. 6; and smallest particles respectively, as previously discussed. In contrast, in the presence of a magnet, the magnetic force dominates over gravity and diffusion. To gain some intuition on the relative strength of the magnetic force on particle motion, the inventors define the ratio of the magnetic force to the drag force and thereby construct a non-dimensional "particle magnetization number".

$$:Mn_p = \frac{|F_{magnetic}|}{|F_{drag}|} = \frac{d_p^2 \cdot VF \cdot \mu_0 M_{sat} |\nabla H|}{18\mu_f |v_f - v_p|}.$$

Figure 2A:
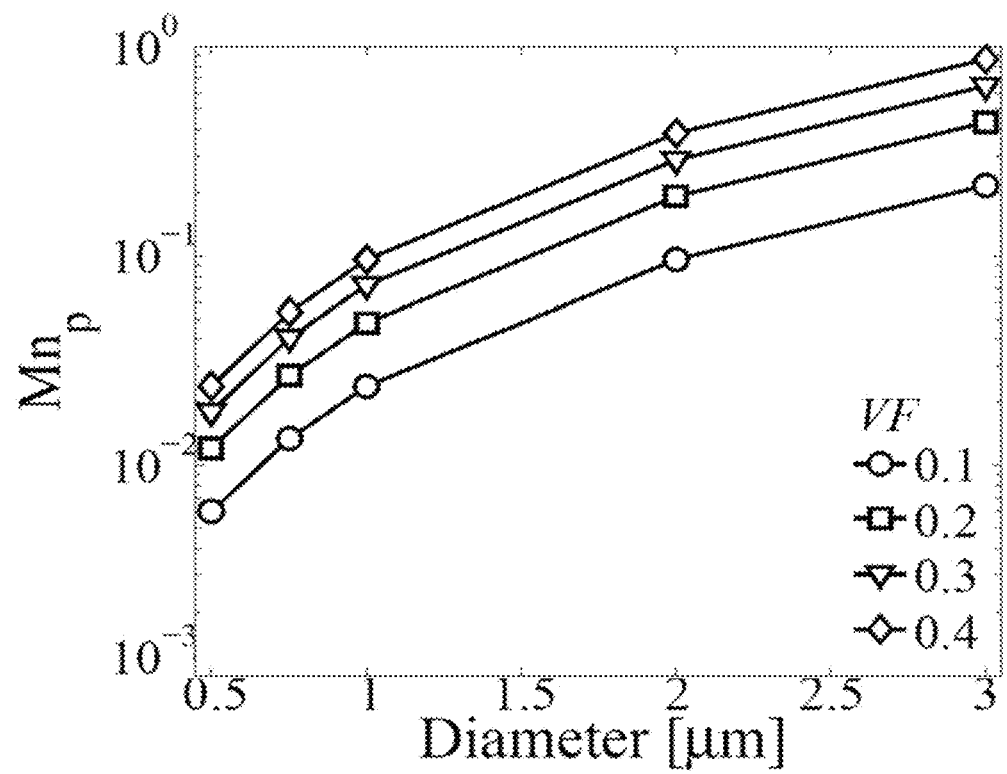
Figure 2B:
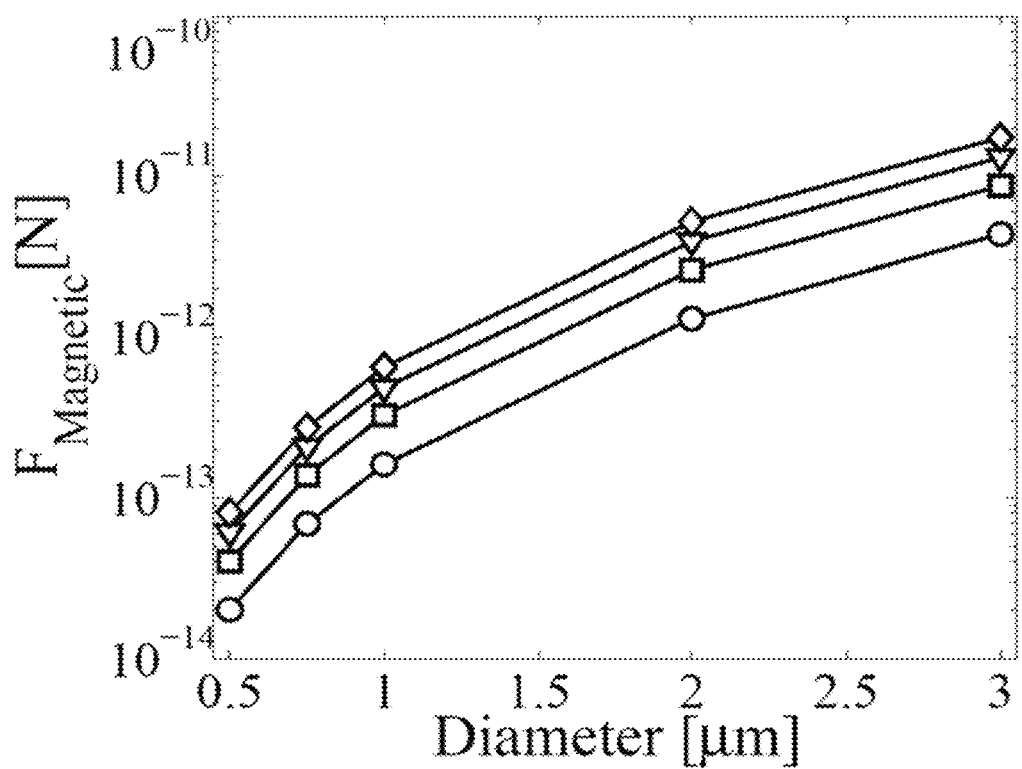

Using $|v_{max}| \approx 0.4$ m/s as the characteristic maximal velocity of the fluid at the domain inlet (retrieved from simulations), the magnitude of $Mn_p$ is plotted in FIG. 2A and the corresponding values of the magnetic force are presented in FIG. 2b (discussed further in the next section). The $Mn_p$ number is plotted against the different particle diameters examined, where the different lines represent the VF loading of SPIONs within droplets. It can be seen from the figure that for the larger particles (e.g., 3 μm and even 2 μm), the magnetic force is on the same order of magnitude as the peak drag force ($Mn_p \sim 0.1$-1). It is thus anticipated that these particles will deposit very quickly in the direction of the magnetic field and will not be transported further into the acinar structure. For the smallest particles, on the other hand, $Mn_p \sim 10^{-2}$ and thus the drag force dominates. Yet, as the air flows towards distal generations, velocities fall quickly both spatially and temporally, thereby increasing the local $Mn_p$. This number increases further once particles enter the alveolar cavity space, where local velocities are known to be several orders of magnitude slower compared to flow in the acinar ducts.

Acinar Deposition

In a first step, the main metric the inventors seek to improve is the drug deposition fraction in the acinus. FIG. 3a presents deposition fractions during the QB maneuver for the various particle types examined; deposition is plotted as a function of particle diameter and the different lines represent varying VF loading of magnetic material in the droplets. It is seen that for particles with $d_p \geq 1$ μm a VF=0.1 is sufficient to deposit nearly all particles. For $d_p$=0.75 μm, a doubling of the VF is needed whereas a fourfold VF increase is required for the smallest particles ($d_p$=0.5 μm).

Hence, for the QB maneuver the amount VF of magnetic material needed for the smaller (<1 μm) particles is quite high, and should preferably be reduced. Hence, the BH1 maneuver was implemented (FIG. 3B), which combines a deeper breath with a BH. Compared to FIG. 3A, it can be sees that with no magnetization (VF=0) all larger particles (2 μm and 3 μm) are now deposited, while the deposition of smaller particles increases about 4-5 fold. This result can be explained due to the fact that diffusion and sedimentation are given longer periods in the absence of convection to yield deposition; it is for this precise reason that a deep inhalation followed by a breath hold is recommended as an effective administration method. In parallel, the influence of the magnetization becomes stronger as well; in FIG. 3b deposition fractions for BH1 with VF=0.025 are comparable to those with VF=0.4 for a QB maneuver (FIG. 3A). Hence, a deep breath combined with a BH maneuver reduces dramatically the amount of magnetic material needed, and thereby the superfluous non-therapeutic material delivered. Comparing now the previous two cases with the BH2 case (FIG. 3C), this latter maneuver is mainly implemented to improve the dispersion of particles across the acinar network, as discussed below. It should be noted that in 3C, despite the reduced magnet operation time, there is only a minor difference in deposition outcomes compared to BH1 (FIG. 3B). It is important to note that the deposition data presented here refers solely to the fraction of particles that deposit relative to those entering the acinar region; this may differ from the aerosol population found initially at the mouth opening.

Particle Dispersion

In parallel to deposition fractions, the inventors next assess the dispersion of the deposited aerosols as indicative of how well particles are able to reach and deposit across the acinar network. Deposition maps are presented in FIG. 4 for representative particle diameters and VFs; particles are colored by the number of neighboring particles within a 50 μm radius (characteristic of the radius of an alveolus), effectively yielding a concentration map. Note that in order to achieve high dispersion, and thus avoid deposition "hot spots", the average number of neighboring particles should be kept low with a uniform distribution across all particles. Looking at the first two rows of FIG. 4 (corresponding to QB), it is first observed that the localized deposition of the larger 3 μm particles (e.g., low dispersion), caused by the magnetic force, as anticipated from the large $Mn_p$ numbers. Note however, that such large particles may also deposit in more proximal airways (e.g., terminal bronchioles) and not necessarily reach the acinus altogether. In contrast to the large particles, magnetized 0.5 μm particles under QB conditions penetrate deeper (though not reaching the distal generations) and deposit in large quantities, thereby dispersing relatively well. However, as seen from FIG. 3A, a relatively high VF is required to achieve high deposition fractions. The 1 μm particles display a transition between the behaviors of the other two particle sizes, where deposition increases but dispersion is now biased towards airway branches aligned with the magnetic field.

The first two rows of FIG. 4 demonstrate that, under QB conditions, due to the superficial inhalation, particles do not have sufficient time to be carried into the most distal branches of the acinus, after crossing the dead space. To overcome this limitation, the patient can be requested to inhale using a slow and deep breath; this deep breath maneuver is incorporated in both BH1 (FIG. 4; third and fourth rows) and BH2 (FIG. 4; fifth row). The third row shows the results of BH1 with VF=0, where a dramatic improvement in penetration depth is witnessed. All particles shown are now able to reach deeper into the acinus, where the smaller particles reach the last acinar generation. Comparing results for BH1 (FIG. 4; third and fourth rows), the dispersion problem is only slightly mollified for the 3 μm particles; the magnetization reduces the dispersion once more and particles deposit quickly before the BH stage. For 0.5 μm particles, both the dispersion and penetration depth are improved when compared to the QB maneuver. Examining the effect of magnetization on these particles, they seem to penetrate as deep but are locally biased towards the magnet. Finally, the 1 μm particles are once again a showcase more representative of a transition between the other two sizes.

The issue of penetration depth is improved through a deep breath maneuver, whereby a reduction of the required magnetic force (required VF) is achieved through the use of a breath hold. Nevertheless, the 3 μm particles still deposit soon after injection, and are not conveyed inside with the deep breath. As mentioned earlier, the BH2 maneuver was hypothesized to improve such outcomes. Comparing the third and fifth rows (note that BH2 with VF=0 is identical to BH1 with VF=0), it is hard to identify noticeable differences by eye. Comparing the fourth and fifth rows, 3 μm particles penetrate much deeper and show better dispersion; these latter particles have reverted to being mainly biased by gravity.

In FIG. 5, a quantification of dispersion is presented, where histograms shown on a logarithmic scale represent the average number of neighbors each particle has (error bars correspond to standard deviations). Statistical significance was calculated using a non-parametric Wilcoxon rank sum test for all pairwise combinations. It should be first mentioned that results for 0.5 μm particles in the QB maneuver are somewhat misleading and must be carefully interpreted since deposition fractions are considerably smaller than unity (approximately 0.7, FIG. 3*a*); in other words, fewer deposited particles lead to lower numbers of neighbors but do not necessarily coincide with better dispersion. Nevertheless, whereas for the 0.5 μm particles it was previously hard to identify differences in the third, fourth and fifth rows of FIG. 4, it is now seen that all three cases have significant differences in dispersion (FIG. 5). Namely, out of the three, VF=0 shows the best results while BH1 with VF=0.025 presents the worst. The 3 μm particles yield the poorest dispersion, with values of the average number of neighbors far exceeding all other particle sizes. This quantification also underlines that the results of BH1 with VF=0 (FIG. 4; third row) and BH2 with VF=0.025 (FIG. 4; fifth row) are indeed similar. Nevertheless, the VF=0 case is slightly better, as particles disperse well in the geometry but are locally pulled towards the magnet (FIG. 4; fifth row). Lastly, it is noted that for 1 μm particles, dispersion under QB with VF=0 is very similar to BH1 with VF=0 (no statistical significance with p=0.68, both cases are marked with tin FIG. 5).

Example 2

Particle Deposition

In this example, the inventors have identified and resolved three of the main prohibiting hurdles that prevented successful magnetic point targeting in the lungs in the past:

(i) Increased deposition near magnet: the magnetic field near the magnet is always stronger than that further away from it. This characteristic has prevented efficient targeting of deep lung locations while avoiding drug deposition in the space between the target and the magnet. To overcome this hurdle, a short-pulsed bolus of aerosolized drugs was implemented, after which the ventilator calculates the volume of air pushed behind the bolus, thus tracking its precise location along the airway path. As a result, this technique guarantees the minimization of airborne particles located in the airways between the magnet and the target, i.e. confining the particles to a bolus rather than a continuous stream (i.e. traditional inhalation) drastically reduces the presence of aerosols in untargeted regions.

(ii) Aerodynamic forces on inhaled particles: The aerodynamic drag forces exerted on airborne particles by inhaled air are orders of magnitude larger than the magnetic force imposed by an external magnet. This mechanism has prevented particles from being captured on site in previous targeting solutions (i.e. deflecting particles off their course within the airflow and depositing them). To solve this issue, a breath-hold maneuver was implement via the ventilator that temporarily annuls the aerodynamic drag force. This thus gives the magnet sufficient time to induce particle deposition (i.e. up to a few seconds).

(iii) Drawbacks of common therapeutic aerosols: Most commonly-inhaled aerosolized medicines (≥1 μm diameter) are specifically intended for efficient deposition. Hence, high particle deposition fractions of common inhalation aerosols limit the targeting ability. To increase the targeting efficiency, namely the deposition ratio between the targeted to untargeted regions, the strategy provided herein revolves around the selection of particles in the specific size range of 90-500 nm. Such aerosols are mostly (~90%) exhaled under normal breathing conditions, and are thus widely considered to be the worst choice for inhalation therapy. Here, the inventors leverage this fundamental characteristic to increase the deposition ratio. Magnetic drug particles located away from the magnet are unaffected by the magnet and will be mostly exhaled.

In the example described herein, the targeting method revolves around the combination of (a) delivering short pulsed bolus comprised of therapeutic aerosols loaded with magnetic particles (e.g., SPIONs), (b) a computer controlled ventilation machine, and (c) an external magnet with a custom-designed magnetic field which guarantees deposition to the target site. Specifically, an optional embodiment of the described solution can be implemented with intubated patients or conscious patients who will be asked to comply, or by measurement of ventilation of flow-rate and volume, such as by use of a spirometer. As a non-limiting example, (i) the smart inhaler releases a short controlled pulse of nebulized medication. The ventilation machine then controls (ii) the volume of air pushed into the lungs, thus tracking the aerosol bolus location. The bolus flows and splits at each airway bifurcation until reaching the targeted location depth. (iii) The ventilator then momentarily halts, leading to a short breath hold. Alternatively, steps (i) and (ii) may be traced and determined under the subjects breathing pattern, using a control unit and a spirometer. During the breath hold, (v) a magnet positioned near the targeted lung region is turned on, i.e. the magnetic field quickly draws the inhaled aerosols closest to it and forces their deposition on the airway walls. The cycle continues with (vi) the reversal of the ventilator thus allowing the patient to exhale the remaining airborne drugs from the untargeted regions (i.e. out of the reach of the magnet), or alternatively—simple exhalation for setups devoid of a ventilator. This cycle described here can be repeated numerous times to increase the dose at the targeted region. FIG. 9 is a flow chart depicting a non-limiting example of the described method.

To further improve the targeting accuracy, an additional controlled-release step can be executed. After the particles are deposited using the previously described targeted delivery method, an additional field (controlled-release field) is used to induce drug release in selected region. For example, an alternating magnetic field can be used to heat the magnetic particles. This allows for the release of the drugs only in the intersection region of the deposited particles and the second controlled-release field. This increased precision method is particularly relevant for targeting in the deep pulmonary acinar regions, where the neighboring branches are denser and harder to target.

Computational fluid dynamics (CFD) simulations were used to investigate particle (e.g., SPION) deposition in upper airways, so as to underline how the magnetic force exerted on particles depends both on the magnitude and gradient of the magnetic field. The magnetic field was designed based on a non-limiting two-opposing solenoid setup. Although this configuration reduced the magnetic field magnitude, it allowed the design of highly localized gradients which were later used to deposit particles (FIG. 7a). The inventors arbitrarily selected to target the right bronchus (solid line in FIG. 7b-c), and managed to achieve a dramatic reduction in the untargeted regions when compared to control state of the art targeting techniques (FIG. 7c).

An experimental system prototype was developed to demonstrate the feasibility and a working proof-of-concept of the disclosed method and device. Briefly, the system incorporates a cast made out of a 3D printed upper airway tree, designed following anatomical measurements. A "smart inhaler" device that delivers the short-pulsed bolus. The custom-designed ventilation machine carries the pulse along the airway tree. This aerosol-loaded pulse has been successfully created and uniformly transported through a tube. The pulse was subsequently stopped (i.e. as in a breath hold) at the desired location resulting in a targeting of a specific desired point (FIG. 8).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An inhalable composition comprising a plurality of inhalable particles; wherein:
   each of said plurality of inhalable particles comprises a magnetic element;
   said magnetic element constitutes from 0.1% to 20% by volume of said inhalable particle;
   said plurality of particles is characterized by an average particle size of between 100 and 750 nm; and said plurality of inhalable particles is in a form of liquid particles; and wherein said inhalable composition is formulated for delivery via inhalation.

2. The inhalable composition of claim 1, wherein said inhalable composition further comprises a therapeutically effective amount of an active agent.

3. The inhalable composition of claim 1, wherein said magnetic element constitutes from 0.1% to 10% by volume of said inhalable particle.

4. The inhalable composition of claim 1, wherein said inhalable composition is formulated for administration to a respiratory tract of a subject.

5. The inhalable composition of claim 3, wherein said administration comprises intratracheobronchial administration, pulmonary administration, or nasal administration, including any combination thereof.

6. The inhalable composition of claim 1, wherein said inhalable composition is in a form of an aerosolized composition, atomized composition, or nebulized composition.

7. The inhalable composition of claim 1, wherein said magnetic element is selected from paramagnetic element or superparamagnetic element.

8. The inhalable composition of claim 1, wherein said magnetic element is selected from the group consisting of: gadolinium, chromium, nickel, copper, iron, manganese, iron oxide (gamma $Fe_2O_3$, and $Fe_3O_4$), and iron hydroxide, or any combination thereof.

9. The inhalable composition of claim 1, wherein said magnetic element is a superparamagnetic iron oxide nanoparticle (SPION).

10. The inhalable composition of claim 2, wherein said active agent is selected from the group consisting of: a therapeutic agent, a prophylactic agent and a diagnostic agent, or a combination thereof; optionally wherein said active agent is a respiratory drug.

11. The inhalable composition of claim 1, wherein each of said inhalable particles is an aqueous droplet.

12. The inhalable composition of claim 1, further comprising a pharmaceutically acceptable carrier.

13. A kit comprising the inhalable composition of claim 1, and an inhaler.

14. The kit of claim 13, wherein said inhalable composition further comprises an active agent.

15. The kit of claim 13, further comprising a control unit adapted for controlling said inhaler so as to adjust any one of inhalation time, inhalation flow rate and inhalation volume.

16. The kit of claim 13, further comprising an external magnet configured for generating a magnetic field so as to facilitate deposition of at least a portion of said inhalable composition within a target site of said subject's respiratory tract.

17. The kit of claim 16, wherein said magnetic field is characterized by a field strength of 0.1 Tesla to 10 Tesla.

18. The kit of claim 13 wherein said inhaler comprises any one of a nebulizer, a dry-powder inhaler, or a metered dose inhaler.

19. The kit of claim 14, wherein said inhalable composition comprises a therapeutically effective amount of the active agent, and wherein said active agent comprises a respiratory drug.

* * * * *